United States Patent
Biadatti et al.

(10) Patent No.: US 7,312,249 B2
(45) Date of Patent: Dec. 25, 2007

(54) VITAMIN D ANALOGUES

(75) Inventors: Thibaud Biadatti, Opio (FR); Etienne Thoreau, Saint Vallier de Thiey (FR); Johannes Voegel, Chateauneuf/Grasse (FR); Andre Jomard, Saint Vallier de Thiey (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 11/066,795

(22) Filed: Feb. 28, 2005

(65) Prior Publication Data

US 2005/0182144 A1 Aug. 18, 2005

Related U.S. Application Data

(63) Continuation of application No. PCT/EP03/10159, filed on Aug. 25, 2003.

(60) Provisional application No. 60/407,716, filed on Sep. 4, 2002.

(30) Foreign Application Priority Data

Aug. 27, 2002 (FR) .................................. 02 10620

(51) Int. Cl.
*A61K 31/59* (2006.01)
*A61K 31/45* (2006.01)
*C07C 43/02* (2006.01)

(52) U.S. Cl. ...................... 514/730; 514/717; 568/662; 568/644; 568/807

(58) Field of Classification Search ................ 514/717; 568/644
See application file for complete search history.

(56) References Cited

U.S. PATENT DOCUMENTS 5,877,342 A 3/1999 Bernardon et al.
6,335,359 B1 * 1/2002 Dalko et al. ................ 514/415
6,689,922 B1 * 2/2004 Bernardon ................... 568/807

FOREIGN PATENT DOCUMENTS

EP 0 776 881 B1 6/1997
EP 0 850 909 B1 7/1998
WO WO 00/26167 A1 5/2000

OTHER PUBLICATIONS

Silverman, Richard B., The Organic Chemistry of Drug Design and Drug Action, 1992, pp. 15-22.*
International Search Report Corresponding to PCT/FR 00/03250 Issued May 7, 2001- 2 Pages.

* cited by examiner

*Primary Examiner*—Rosalynd Keys
(74) *Attorney, Agent, or Firm*—Buchanan, Ingersoll & Rooney, PC

(57) ABSTRACT

Novel biaromatic vitamin D analogues have the general formula (I):

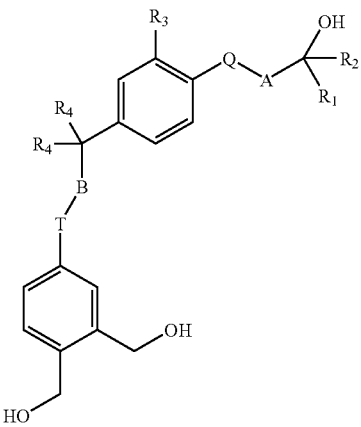

and are suited for a wide variety of pharmaceutical applications, whether in human or veterinary medicine, and also for cosmetic applications.

29 Claims, 1 Drawing Sheet

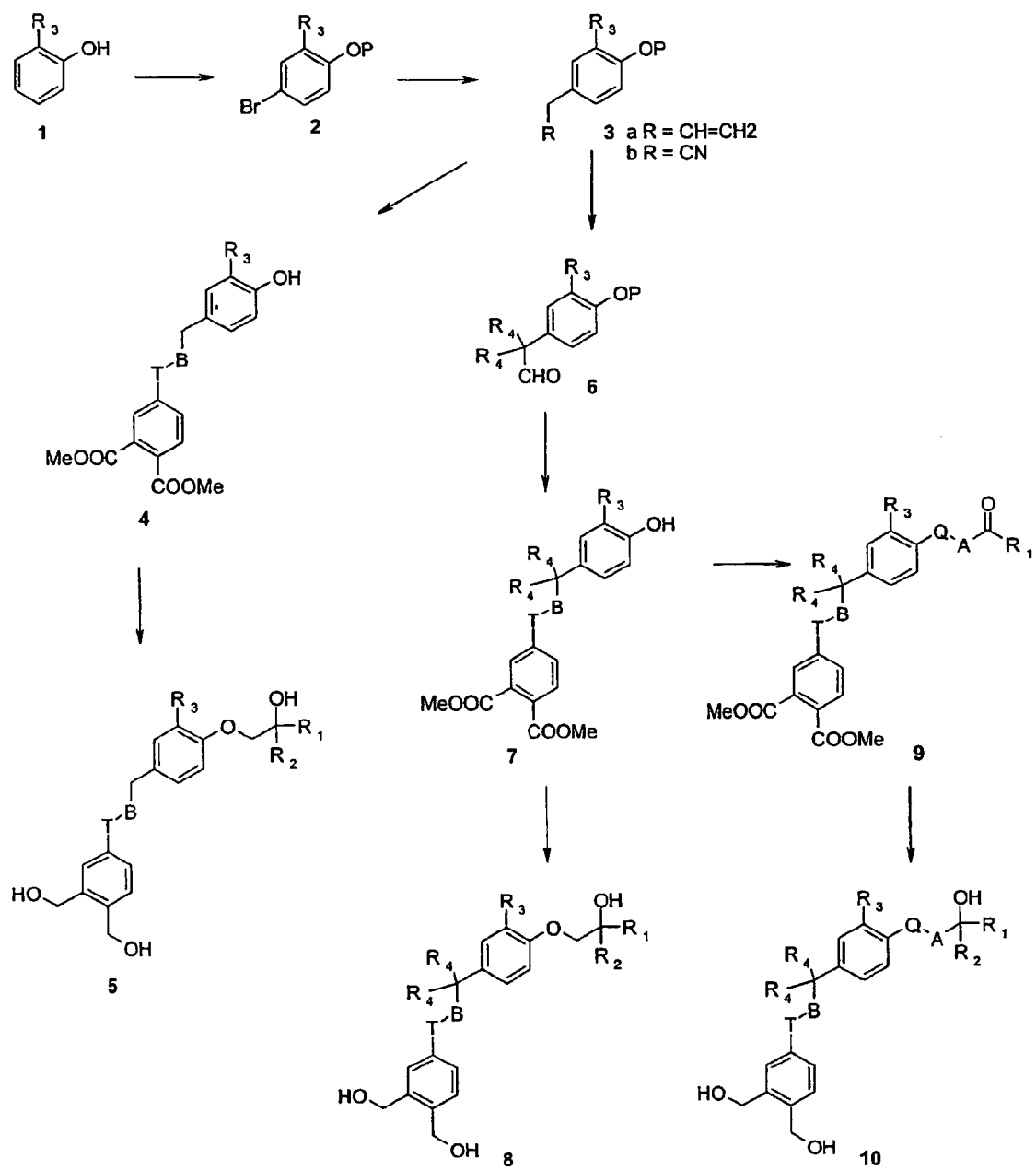

VITAMIN D ANALOGUES

CROSS-REFERENCE TO PRIORITY/PCT/PROVISIONAL APPLICATIONS

This application claims priority under 35 U.S.C. § 119 of FR-02/10620, filed Aug. 27, 2002, and of provisional application Ser. No. 60/407,716, filed Sep. 4, 2002, and is a continuation of PCT/EP 2003/010159, filed Aug. 25, 2003 and designating the United States (published in the English language on Mar. 11, 2004 as WO 2004/020379 A1), each hereby expressly incorporated by reference and each assigned to the assignee hereof.

BACKGROUND OF THE INVENTION

1. Technical Field of the Invention

The present invention relates to novel biaromatic compounds which are analogues of vitamin D.

The present invention also relates to the process for their preparation and their formulation into pharmaceutical compositions suited for applications in human or veterinary medicine, or, alternatively, formulated into cosmetic compositions.

The novel family of compounds according to the invention includes compounds which have a marked activity in the fields of cell differentiation and proliferation and find applications, more particularly, in the topical and systemic treatment of dermatological conditions (and the like) linked to a keratinization disorder, of conditions with an inflammatory and/or immunoallergic components and of hyperproliferation of tissues of ectodermal origin (skin, epithelium and the like), whether benign or malignant. These compounds may, in addition, be administered to combat skin aging, whether photoinduced or chronologic, and to treat cicatrization disorders.

It is also possible to use the compounds according to the invention in cosmetic compositions for body and hair hygiene.

2. Description of Background and/or Related and/or Prior Art

Vitamin D is an essential vitamin for the prevention and treatment of defects in the mineralization of cartilage (rickets), and of bone (osteomalacia), and even of certain forms of osteoporosis in the elderly subject. However, it is now accepted that its functions extend well beyond the regulation of bone metabolism and of calcium homeostasis. Among these, there may be mentioned its actions on cell proliferation and differentiation and the control of the immune defenses. Their discovery has paved the way for new therapeutic approaches in dermatology, cancerology as well as in the field of autoimmune diseases and that of organ and tissue transplants.

An effective therapeutic application has for long been hampered by the toxicity of this vitamin (hypercalcaemia which is sometimes fatal). Currently, structural analogues of vitamin D are synthesized, certain of which conserve only the differentiating properties and have no action on calcium metabolism.

WO 00/10958 describes vitamin D3-mimetic nonsecosteroidal biaromatic compounds, which are ligands for the VDR receptor. These compounds find applications in the treatment of pathologies linked to the deregulation of calcium metabolism. However, the general structure of these compounds is substantially different from that of the compounds of the present invention; indeed, the two aromatic rings of the compounds described in WO 00/10958 are linked to each other by a carbon atom whereas for the compounds of this invention, the two aromatic rings are linked by a chain comprising three atoms.

Likewise, WO 00/26167 and WO 01/38320 propose bicyclic compounds which are analogues of vitamin D and WO 01/38303 describes triaromatic compounds which are also analogues of vitamin D. These three classes of compounds exhibit, here again, chemical structures which are quite different from that of the compounds of the present invention.

SUMMARY OF THE INVENTION

A novel family of compounds has now been developed which compounds are analogues of vitamin D, exhibiting a marked biological activity, in particular in tests for activity on the differentiation of HL60 cells and for proliferation of human keratinocytes, and in the test for VDR agonist activity.

Thus, the present invention features novel compounds having the following general formula (I);

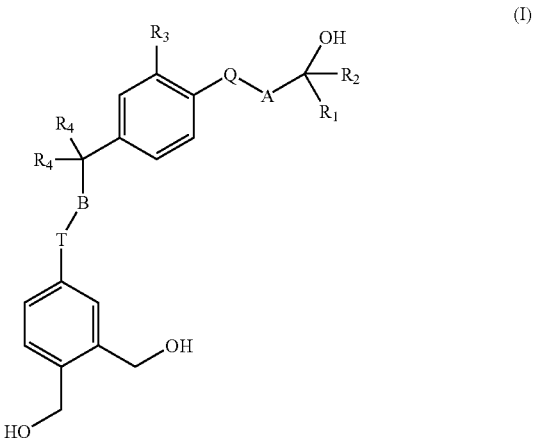

in which A-Q is an unsubstituted alkyne or alkene bond, a —$CH_2$—O— radical, a —$CH_2$—S— radical or —$CH_2$—$CH_2$— radical; B-T is an unsubstituted alkyne or alkene bond, a —$CH_2$—S—, —$CH_2$—O—, —$CH_2$—$CH_2$— or —$CH_2$—$NR_6$— radical; $R_6$ is as defined below; $R_1$ and $R_2$, which may be identical or different, are each a hydrogen atom, a linear or branched alkyl radical having 1 to 5 carbon atoms, or the radical —$CF_2R_5$; $R_3$ is a linear or branched alkyl radical having 1 to 5 carbon atoms, or the radical $CF_2R_5$; $R_5$ is as defined below; the radicals $R_4$, which may be identical, are each a hydrogen atom, a linear or branched alkyl radical having 1 to 6 carbon atoms, or the radical —$CF_2R_5$, with the proviso that the two radicals may also form a saturated ring having 4 to 7 carbon atoms, or a saturated heterocycle such as furan, pyran, pyrrolidine substituted on the nitrogen heteroatom with a radical $R_7$ or piperidine substituted on the nitrogen heteroatom with a radical $R_7$; $R_7$ is as defined below; $R_5$ is a fluorine atom, a hydrogen atom, or a radical —$CF_3$; $R_6$ is a hydrogen atom, a linear or branched alkyl radical having 1 to 6 carbon atoms, or the radical —$C(O)R_8$; $R_8$ is as defined below; $R_7$ and $R_8$, which may be identical or different, are each a hydrogen atom, or a linear or branched alkyl radical having 1 to 6 carbon atoms; and the optical and geometric isomers and salts thereof.

BRIEF DESCRIPTION OF THE DRAWINGS

The FIGURE of Drawing illustrates a variety of reaction sequences suited for the synthesis of the compounds of the invention.

DETAILED DESCRIPTION OF BEST MODE AND SPECIFIC/PREFERRED EMBODIMENTS OF THE INVENTION

The present invention embraces mixtures of optical isomers and geometrical isomers, including racemic mixtures.

In the case of the compounds described above comprising a nitrogen atom, the present invention also relates to these compounds when they are in the form of cosmetically or pharmaceutically acceptable salts, as salts of an inorganic or organic acid, in particular hydrochloric, sulphuric, acetic, fumaric, hemisuccinic, maleic and mandelic acid.

The expression linear or branched alkyl radical having 1 to 5 carbon atoms is understood to mean, preferably, a methyl, ethyl, n-propyl, i-propyl, n-butyl, i-butyl, t-butyl, n-pentyl, 1-methylbutyl, 3-methylbutyl or 2,2-dimethylbutyl radical.

The expression linear or branched alkyl radical having 1 to 6 carbon atoms is understood to mean, preferably, a methyl, ethyl, n-propyl, i-propyl, n-butyl, i-butyl, t-butyl, n-pentyl, 1-methylbutyl, 3-methylbutyl, 2,2-dimethylpropyl, n-hexyl, 4-methylpentyl or 3,3-dimethylbutyl radical.

The expression saturated ring having 4 to 7 carbon atoms is understood to mean a cyclobutyl, a cyclopentyl, a cyclohexyl or a cycloheptyl ring member.

Among the compounds of formula (I) falling within the scope of the present invention, the following are particularly exemplary:

1. 1-{4-[3-(3,4-Bis-hydroxymethyl-phenyl)-propyl]-2-ethyl-phenoxy]-3,3-dimethyl-butan-2-ol;
2. 1-{4-[3-(3,4-Bis-hydroxymethyl-phenyl)-propyl]-2-methyl-phenoxy]-3,3-dimethyl-butan-2-ol;
3. (4-{3-[3-ethyl-4-(2-ethyl-2-hydroxy-butoxy)-phenyl]-propyl}-2-hydroxymethyl-phenyl)-methanol;
4. (4-{3-[4-(2-ethyl-2-hydroxy-butoxy)-3-methyl-phenyl]-propyl}-2-hydroxymethyl-phenyl)-methanol;
5. (2-hydroxymethyl-4-{3-[4-(2-hydroxy-3-methyl-phenyl-butoxy)-3-methyl-phenyl]-propyl}-phenyl)-methanol;
6. (4-{3-[3-ethyl-4-(2-hydroxy-3-methyl-butoxy)-phenyl]-propyl}-2-hydroxymethyl-phenyl)-methanol;
7. (2-hydroxymethyl-4-{3-[4-(2-hydroxy-3-methyl-butylsulphanyl)-3-methyl-phenyl]-propyl-phenyl)-methanol;
8. (4-{3-[3-ethyl-4-(2-hydroxy-3-methyl-butylsulphanyl)-phenyl]-propyl)-2-hydroxymethyl-phenyl)-methanol;
9. (2-hydroxymethyl-4-{3-[4-(3-hydroxy-4-methyl-pentyl)-3-methyl-phenyl]-propyl}-phenyl)-methanol;
10. (4-{3-[3-ethyl-4-(3-hydroxy-4-methyl-pentyl)-phenyl]-propyl}-2-hydroxymethyl-phenyl)-methanol;
11. (E)-1-{4-[3-(3,4-bis-hydroxymethyl-phenyl)-propyl]-2-methyl-phenyl}-4-methyl-pent-1-en-3-ol;
12. (E)-1-{4-[3-(3,4-bis-hydroxymethyl-phenyl)-propyl-2-ethyl-phenyl}-4-methyl-pent-1-en-3-ol;
13. (4-{3-[4-(2-hydroxy-3,3-dimethyl-butylsulphanyl)-3-methyl-phenyl]-propyl}-2-hydroxymethyl-phenyl)-methanol;
14. (4-{3-[3-ethyl-4-(2-hydroxy-3,3-dimethyl-butylsulphanyl)-phenyl]-propyl)-2-hydroxymethyl-phenyl)-methanol;
15. (4-{3-[4-(3-hydroxy-4,4-dimethyl-pentyl)-3-methyl-phenyl]-propyl}-2-hydroxymethyl-phenyl)-methanol;
16. (4-{3-[3-ethyl-4-(3-hydroxy-4,4-dimethyl-pentyl)-phenyl]-propyl}-2-hydroxymethyl-phenyl)-methanol;
17. (E)-1-{4-[3-(3,4-bis-hydroxymethyl-phenyl)-propyl]-2-methyl-phenyl}-4,4-dimethyl-pent-1-en-3-ol;
18. (E)-1-{4-[3-(3,4-bis-hydroxymethyl-phenyl)-propyl]-2-ethyl-phenyl}-4,4-dimethyl-pent-1-en-3-ol;
19. (2-hydroxymethyl-4-{3-[3-methyl-4-)(3,3,3-trifluoro-2-hydroxy-propoxy)-phenyl]-propyl}-phenyl)-methanol;
20. (4-{3-[3-ethyl-4-(3,3,3-trifluoro-2-hydroxy-propoxy)-phenyl]-propyl}-2-hydroxymethyl-phenyl)-methanol;
21. (2-hydroxymethyl-4-{3-[3-methyl-4-(3,3,3-trifluoro-2-hydroxy-propylsulphanyl)-phenyl]-propyl)-phenyl)-methanol;
22. (4-{3-[3-ethyl-4-(3,3,3-trifluoro-2-hydroxy-propylsulphanyl)-phenyl]-propyl}-2-hydroxymethyl-phenyl)-methanol;
23. (2-hydroxymethyl-4-{3-[3-methyl-4-(4,4,4-trifluoro-3-hydroxy-butyl)-phenyl]-propyl}-phenyl)-methanol;
24. (4-{3-[3-ethyl-4-(4,4,4-trifluoro-3-hydroxy-butyl)-phenyl]-propyl}-2-hydroxymethyl-phenyl)-methanol;
25. (2-hydroxymethyl-4-{3-[3-methyl-4-((E)-4,4,4-trifluoro-3-hydroxy-but-1-enyl)-phenyl]-propyl}phenyl)-methanol;
26. (4-{3-[3-ethyl-4-((E)-4,4,4-trifluoro-3-hydroxy-but-1-enyl)-phenyl]-propyl}-2-hydroxymethyl-phenyl)-methanol;
27. (2-hydroxymethyl-4-{3-[3-methyl-4-(4,4,4-trifluoro-2-hydroxy-3-trifluoromethyl-butoxy)-phenyl]-propyl}-phenyl)-methanol;
28. (4-{3-[3-ethyl-4-(4,4,4-trifluoro-2-hydroxy-3-trifluoromethyl-butoxy)-phenyl]-propyl)-2-hydroxymethyl-phenyl)-methanol;
29. (2-hydroxymethyl-4-{3-[3-methyl-4-(4,4,4-trifluoro-2-hydroxy-3-trifluoromethyl-butylsulphanyl)-phenyl]-propyl}-phenyl)-methanol;
30. (4-{3-[3-ethyl-4-(4,4,4-trifluoro-2-hydroxy-3-trifluoromethyl-butylsulphanyl)-phenyl]-propyl}-2-hydroxymethyl-phenyl)-methanol;
31. (2-hydroxymethyl-4-{3-[methyl-(5,5,5-trifluoro-3-hydroxy-4-trifluoromethyl-pentyl)-phenyl]-propyl}-phenyl)-methanol;
32. (4-{3-[ethyl-(5,5,5-trifluoro-3-hydroxy-4-trifluoromethyl-pentyl)-phenyl]-propyl}-2-hydroxymethyl-phenyl)-methanol;
33. (E)-{4-[3-(3,4-bis-hydroxymethyl-phenyl)-propyl]-2-methyl-phenyl}-5,5,5-trifluoro-4-trifluoromethyl-pent-1-en-3-ol;
34. (E)-{4-[3-(3,4-bis-hydroxymethyl-phenyl)-propyl]-2-ethyl-phenyl}-5,5,5-trifluoro-4-trifluoromethyl-pent-1-en-3-ol;
35. (2-hydroxymethyl-4-{3-[4-(2-hydroxy-3-methyl-butoxy)-3-methyl-phenyl]-3-methyl-butyl}-phenyl)-methanol;
36. (4-{3-[3-ethyl-4-(2-hydroxy-3-methyl-butoxy)phenyl]-3-methyl-butyl}-2-hydroxymethyl-phenyl)-methanol;
37. (2-hydroxymethyl-4-{3-[4-(2-hydroxy-3-methyl-butylsulphanyl)-3-methyl-phenyl]-3-methyl-butyl}-phenyl)-methanol;
38. (4-{3-[3-ethyl-4-(2-hydroxy-3-methyl-butylsulphanyl)-phenyl]-3-methyl-butyl}-2-hydroxymethyl-phenyl)-methanol;
39. (2-hydroxymethyl-4-{3-[4-(3-hydroxy-4-methyl-pentyl)-3-methyl-phenyl]-3-methyl-butyl}-phenyl)-methanol;
40. (4-{3-[3-ethyl-4-(3-hydroxy-4-methyl-pentyl)-phenyl]-3-methyl-butyl}-2-hydroxymethyl-phenyl)-methanol;

41. (E)-1-{4-[3-(3,4-bis-hydroxymethyl-phenyl)-1,1-dimethyl-propyl]-2-methyl-phenyl}-4-methyl-pent-1-en-3-ol;
42. (E)-1-{4-[3-(3,4-bis-hydroxymethyl-phenyl)-1,1-dimethyl-propyl]-2-ethyl-phenyl}-4-methyl-pent-1-en-3-ol;
43. (4-{3-[4-(2-hydroxy-3,3-dimethyl-butoxy)-3-methyl-phenyl]-3-methyl-butyl}-2-hydroxymethyl-phenyl)-methanol;
44. (4-{3-[3-ethyl-4-(2-hydroxy-3,3-dimethyl-butoxy)-phenyl]-3-methyl-butyl}-2-hydroxymethyl-phenyl)-methanol;
45. (4-{3-[4-(2-hydroxy-3,3-dimethyl-butylsulphanyl)-3-methyl-phenyl]-3-methyl-butyl}-2-hydroxymethyl-phenyl)-methanol;
46. (4-{3-[3-ethyl-4-(2-hydroxy-3,3-dimethyl-butylsulphanyl)-phenyl]-3-methyl-butyl}-2-hydroxymethyl-phenyl)-methanol;
47. (4-{3-[4-(3-hydroxy-4,4-dimethyl-pentyl)-3-methyl-phenyl]-3-methyl-butyl}-2-hydroxymethyl-phenyl)-methanol;
48. (4-{3-[3-ethyl-4-(3-hydroxy-4,4-dimethyl-pentyl)-phenyl]-3-methyl-butyl}-2-hydroxymethyl-phenyl)-methanol;
49. (E)-1-{4-[3-(3,4-bis-hydroxymethyl-phenyl)-1,1-dimethyl-propyl]-2-methyl-phenyl}-4,4-dimethyl-pent-1-en-3-ol;
50. (E)-1-{4-[3-(3,4-bis-hydroxymethyl-phenyl)-1,1-dimethyl-propyl]-2-ethyl-phenyl}-4,4-dimethyl-pent-1-en-3-ol;
51. (4-{3-ethyl-3-[4-(2-hydroxy-3-methyl-butoxy)3-methyl-phenyl]-pentyl-2-hydroxymethyl-phenyl)-methanol;
52. (4-{3-ethyl-3-[3-ethyl-4-(2-hydroxy-3-methyl-butoxy)-phenyl]-pentyl}-2-hydroxymethyl-phenyl)-methanol;
53. (4-{3-ethyl-3-[4-(2-hydroxy-3-methyl-butylsulphanyl)-3-methyl-phenyl]-pentyl}-2-hydroxymethyl-phenyl)-methanol;
54. (4-{3-ethyl-3-[3-ethyl-4-(2-hydroxy-3-methyl-butylsulphanyl)-phenyl]-pentyl}-2-hydroxymethyl-phenyl)-methanol;
55. (4-{3-ethyl-3-[4-(3-hydroxy-4-methyl-pentyl)-3-methyl-phenyl]-pentyl}-2-hydroxymethyl-phenyl)-methanol;
56. (4-{3-ethyl-3-[3-ethyl-4-(3-hydroxy-4-methyl-pentyl)-phenyl]-pentyl}-2-hydroxymethyl-phenyl)-methanol;
57. (E)-1-{4-[3-(3,4-bis-hydroxymethyl-phenyl)-1,1-diethyl-propyl]-2-methyl-phenyl}-4-methyl-pent-1-en-3-ol;
58. (E)-1-{4-[3-(314-bis-hydroxymethyl-phenyl)-1,1-diethyl-propyl]-2-ethyl-phenyl}-4-methyl-pent-1-en-3-ol;
59. (4-{3-ethyl-3-[4-(2-hydroxy-3,3-dimethyl-butoxy)-3-methyl-phenyl]-pentyl}-2-hydroxymethyl-phenyl)-methanol;
60. (4-{3-ethyl-3-[3-ethyl-4-(2-hydroxy-3,3-dimethyl-butoxy)-phenyl]-pentyl}-2-hydroxymethyl-phenyl)-methanol;
61. (4-{3-ethyl-3-[4-(2-hydroxy-3,3-dimethyl-butylsulphanyl)-3-methyl-phenyl]-pentyl}-2-hydroxymethyl-phenyl)-methanol;
62. (4-{3-ethyl-3-[3-ethyl-4-(2-hydroxy-3,3-dimethyl-butylsulphanyl)-phenyl]-pentyl}-2-hydroxymethyl-phenyl)-methanol;
63. 4-{3-ethyl-3-[4-(3-hydroxy-4,4-dimethyl-pentyl)-3-methyl-phenyl]-pentyl}-2-hydroxymethyl-phenyl)-methanol;
64. (4-{3-ethyl-3-[3-ethyl-4-(3-hydroxy-4,4-dimethyl-pentyl)-phenyl]-pentyl}-2-hydroxymethyl-phenyl)-methanol;
65. (E)-1-{4-[3-(3,4-bis-hydroxymethyl-phenyl)-1,1-diethyl-propyl]-2-methyl-phenyl}-4,4-dimethyl-pent-1-en-3-ol;
66. (E)-I-{4-[3-(3,4-bis-hydroxymethyl-phenyl)-1,1-diethyl-propyl]-2-ethyl-phenyl}-4,4-dimethyl-pent-1-en-3-ol;
67. [2-hydroxymethyl-4-(2-{1-[4-(2-hydroxy-3-methyl-butoxy)-3-methyl-phenyl]-cyclopentyl}-ethyl)-phenyl]-methanol;
68. [4-(2-{1-[3-ethyl-4-(2-hydroxy-3-methyl-butoxy)-phenyl]-cyclopentyl}-ethyl)-2-hydroxymethyl-phenyl]-methanol;
69. [2-hydroxymethyl-4-(2-{1-[4-(2-hydroxy-3-methyl-butylsulphanyl)-3-methyl-phenyl]-cyclopentyl}-ethyl)-phenyl]-methanol;
70. [4-(2-{1-[3-ethyl-4-(2-hydroxy-3-methyl-butylsulphanyl)-phenyl]-cyclopentyl}-ethyl)-2-hydroxymethyl-phenyl]-methanol;
71. [2-hydroxymethyl-4-(2-{I-[4-(3-hydroxy-4-methyl-pentyl)-3-methyl-phenyl]-cyclopentyl}-ethyl)-phenyl]-methanol;
72. [4-(2-{1-[3-ethyl-4-(3-hydroxy-4-methyl-pentyl)-phenyl]-cyclopentyl}-ethyl)-2-hydroxymethyl-phenyl]-methanol;
73. (E)-1-(4-{1-[2-(3,4-bis-hydroxymethyl-phenyl)-ethyl]-cyclopentyl}-2-methyl-phenyl)-4-methyl-pent-1-en-3-ol;
74. (E)-1-(4-{1-[2-(3,4-bis-hydroxymethyl-phenyl)-ethyl]-cyclopentyl}-2-ethyl-phenyl)-4-methyl-pent-1-en-3-ol;
75. [4-(2-{1-[4-(2-hydroxy-3,3-dimethyl-butoxy)-3-methyl-phenyl]-cyclopentyl}-ethyl)-2-hydroxymethyl-phenyl]-methanol;
76. [4-(2-{1-[3-ethyl-4-(2-hydroxy-3,3-dimethyl-butoxy)-phenyl]-cyclopentyl}-ethyl)-2-hydroxymethyl-phenyl]-methanol;
77. [4-(2-{1-[4-(2-hydroxy-3,3-dimethyl-butylsulphanyl-3-methyl-phenyl]-cyclopentyl}-ethyl)-2-hydroxymethyl-phenyl]-methanol;
78. [4-(2-{1-[3-ethyl-4-(2-hydroxy-3,3-dimethyl-butylsulphanyl)-phenyl]-cyclopentyl}-ethyl)-2-hydroxymethyl-phenyl]-methanol;
79. [4-(2-{1-[4-(3-hydroxy-4,4-dimethyl-pentyl)-3-methyl-phenyl]-cyclopentyl}-ethyl)-2-hydroxymethyl-phenyl]-methanol;
80. [4-(2-{1-[3-ethyl-4-(3-hydroxy-4,4-dimethyl-pentyl)-phenyl]-cyclopentyl}-ethyl)-2-hydroxymethyl-phenyl]-methanol;
81. (E)-1-(4-{1-[2-(3,4-bis-hydroxymethyl-phenyl)-ethyl]-cyclopentyl}-2-methyl-phenyl)-4,4-dimethyl-pent-1-en-3-ol;
82. (E)-1-(4-{1-[2-(3,4-bis-hydroxymethyl-phenyl)-ethyl]-cyclopentyl}-2-ethyl-phenyl)-4,4-dimethyl-pent-1-en-3-ol;
83. [2-hydroxymethyl-4-(2-{1-[4-(2-hydroxy-3-methyl-butoxy)-3-methyl-phenyl]-cyclohexyl}-ethyl)-phenyl]-methanol;
84. [4-(2-{1-[3-ethyl-4-(2-hydroxy-3-methyl-butoxy)-phenyl]-cyclohexyl}-ethyl)-2-hydroxymethyl-phenyl]-methanol;
85. [2-hydroxymethyl-4-(2-{1-[4-(2-hydroxy-3-methy-butylsulphanyl)-3-methyl-phenyl]-cyclohexyl}-ethyl)-phenyl]-methanol;
86. [4-(2-{1-[3-ethyl-4-(2-hydroxy-3-methyl-butylsulphanyl)-phenyl]-cyclohexyl}-ethyl)-2-hydroxymethyl-phenyl]-methanol;
87. [2-hydroxymethyl-4-(2-{1-[4-(3-hydroxy-4-methyl-pentyl)-3-methyl-phenyl]-cyclohexyl}-ethyl)-phenyl]-methanol;

88. [4-(2-{1-[3-ethyl-4-(3-hydroxy-4-methyl-pentyl)-phenyl]-cyclohexyl}-ethyl)-2-hydroxymethyl-phenyl]-methanol;
89. (E)-1-(4-{1-[2-(3,4-bis-hydroxymethyl-phenyl)-ethyl]-cyclohexyl}-2-methyl-phenyl)-4-methyl-pent-1-en-3-ol;
90. (E)-1-(4-{1-[2-(3,4-bis-hydroxymethyl-phenyl)-ethyl]-cyclohexyl}-2-ethyl-phenyl)-4-methyl-pent-1-en-3-ol;
91. [4-(2-{1-[4-(2-hydroxy-3,3-dimethyl-butoxy)-3-methyl-phenyl]-cyclohexyl}-ethyl)-2-hydroxymethyl-phenyl]-methanol;
92. [4-(2-{1-[3-ethyl-4-(2-hydroxy-3,3-dimethyl-butoxy)-phenyl]-cyclohexyl}-ethyl)-2-hydroxymethyl-phenyl]-methanol;
93. [4-(2-{1-[4-(2-hydroxy-3,3-dimethyl-butylsulphanyl)-3-methyl-phenyl]-cyclohexyl}-ethyl)-2-hydroxymethyl-phenyl]-methanol;
94. [4-(2-{1-[3-ethyl-4-(2-hydroxy-3,3-dimethyl-butylsulphanyl)-phenyl]-cyclohexyl}-ethyl)-2-hydroxymethyl-phenyl]-methanol;
95. [4-(2-{1-[4-(3-hydroxy-4,4-dimethyl-pentyl)-3-methyl-phenyl]-cyclohexyl}-ethyl)-2-hydroxymethyl-phenyl]-methanol;
96. [4-(2-{1-[3-ethyl-4-(3-hydroxy-4,4-dimethyl-pentyl)-phenyl]-cyclohexyl}-ethyl)-2-hydroxymethyl-phenyl]-methanol;
97. (E)-1-(4-{1-[2-(3,4-bis-hydroxymethyl-phenyl)-ethyl]-cyclohexyl}-2-methyl-phenyl)-4,4-dimethyl-pent-1-en-3-ol;
98. (E)-1-(4-{1-[2-(3,4-bis-hydroxymethyl-phenyl)-ethyl]-cyclohexyl}-2-ethyl-phenyl)-4,4-dimethyl-pent-1-en-3-ol;
99. (4-{2-ethyl-2-[4-(2-hydroxy-3-methyl-butoxy)-3-methyl-phenyl]-butoxy}-2-hydroxymethyl-phenyl)-methanol;
100. (4-{2-ethyl-2-[3-ethyl-4-(2-hydroxy-3-methyl-butoxy)-phenyl]-butoxy}-2-hydroxymethyl-phenyl)-methanol;
101. (4-{2-ethyl-2-[4-(2-hydroxy-3-methyl-butylsulphanyl)-3-methyl-phenyl]-butoxy}-2-hydroxymethyl-phenyl)-methanol;
102. (4-{2-ethyl-2-[3-ethyl-4-(2-hydroxy-3-methyl-butylsulphanyl)-phenyl]-butoxy}-2-hydroxymethyl-phenyl)-methanol;
103. (4-{2-ethyl-2-[4-(3-hydroxy-4-methyl-pentyl)-3-methyl-phenyl]-butoxy}-2-hydroxymethyl-phenyl)-methanol;
104. (4-{2-ethyl-2-[3-ethyl-4-(3-hydroxy-4-methyl-pentyl)-phenyl]-butoxy}-2-hydroxymethyl-pentyl)-methanol;
105. (E)-1-{4-[1-(3,4-bis-hydroxymethyl-phenoxymethyl)-1-ethyl-propyl]-2-methyl-phenyl}-4-methyl-pen-1-en-3-ol;
106. (E)-1-{4-[1-(3,4-bis-hydroxymethyl-phenoxymethyl)-1-ethyl-propyl]-2-ethyl-phenyl}-4-methyl-pen-1-en-3-ol;
107. (4-{2-ethyl-2-[4-(2-hydroxy-3,3-dimethyl-butoxy)-3-methyl-phenyl]-butoxy}-2-hydroxymethyl-phenyl)-methanol;
108. (4-{2-ethyl-2-[3-ethyl-4-(2-hydroxy-3,3-dimethyl-butoxy)-phenyl]-butoxy}-2-hydroxymethyl-phenyl)-methanol;
109. (4-{2-ethyl-2-[4-(2-hydroxy-3,3-dimethyl-butylsulphanyl)-3-methyl-phenyl]-butoxy}-2-hydroxymethyl-phenyl)-methanol;
110. (4-{2-ethyl-2-[3-ethyl-4-(2-hydroxy-3,3-dimethyl-butylsulphanyl)-phenyl]-butoxy}-2-hydroxymethyl-phenyl)-methanol;
111. (4-{2-ethyl-2-[4-(3-hydroxy-4,4-dimethyl-pentyl)-3-methyl-phenyl]-butoxy}-2-hydroxymethyl-phenyl)-methanol;
112. (4-{2-ethyl-2-[3-ethyl-4-(3-hydroxy-4,4-dimethyl-pentyl)-phenyl]-butoxy}-2-hydroxymethyl-phenyl)-methanol;
113. (E)-1-{4-[1-(3,4-bis-hydroxymethyl-phenoxymethyl)-1-ethyl-propyl]-2-methyl-phenyl}-4,4-dimethyl-pent-1-en-3-ol;
114. (E)-1-{4-[1-(3,4-bis-hydroxymethyl-phenoxymethyl)-1-ethyl-propyl]-2-ethyl-phenyl}-4,4-dimethyl-pent-1-en-3-ol;
115. (4-{(E)-3-ethyl-3-[4-2-hydroxy-3-methyl-butoxy)-3-methyl-phenyl]-pent-1-enyl}-2-hydroxymethyl-phenyl)-methanol;
116. (4-{(E)-3-ethyl-3-[3-ethyl-4-(2-hydroxy-3-methyl-butoxy)-phenyl]-pent-1-enyl}-2-hydroxymethyl-phenyl)-methanol;
117. (4-{(E)-3-ethyl-3-[4-(2-hydroxy-3-methyl-butylsulphanyl)-3-methyl-phenyl]-pent-1-enyl}-2-hydroxymethyl-phenyl)-methanol;
118. (4-{(E)-3-ethyl-3-[3-ethyl-4-(2-hydroxy-3-methyl-butylsulphanyl)-phenyl]-pent-1-enyl}-2-hydroxymethyl-phenyl)-methanol;
119. (4-{(E)-3-ethyl-3-[4-(3-hydroxy-4-methyl-pentyl)-3-methyl-phenyl]-pent-1-enyl}-2-hydroxymethyl-phenyl)-methanol;
120. (4-{(E)-3-ethyl-3-[3-ethyl-4-(3-hydroxy-4-methyl-pentyl)-phenyl]-pent-1-enyl}-2-hydroxymethyl-phenyl)-methanol;
121. (E)-1-{4-[(E)-3-(3,4-bis-hydroxymethyl-phenyl)-1,1-diethyl-allyl]-2-methyl-phenyl}-4-methyl-pent-1-en-3-ol;
122. (E)-1-{4-[(E)-3-(3,4-bis-hydroxymethyl-phenyl)-1,1-diethyl-allyl]-2-ethyl-phenyl}-4-methyl-pent-1-en-3-ol;
123. (4{(E)-3-ethyl-3-3[4-(2-hydroxy-3,3-dimethyl-butoxy)-3-methyl-phenyl]pent-1-enyl}-2-hydroxymethyl-phenyl)-methanol;
124. (4-{(E)-3-ethyl-3-[3-ethyl-4-(2-hydroxy-3,3-dimethyl-butoxy)-phenyl]-pent-1-enyl}-2-hydroxymethyl-phenyl)-methanol;
125. (4-{(E)-3-ethyl-3-[4-(2-hydroxy-3,3-dimethyl-butylsulphanyl)3-methyl-phenyl]-pent-1-enyl}-2-hydroxymethyl-phenyl)-methanol;
126. (4-{(E)-3-ethyl-3-[3-ethyl-4-(2-hydroxy-3,3-dimethyl-butylsulphanyl)-phenyl]-pent-1-enyl}-2-hydroxymethyl-phenyl)-methanol;
127. (4-{(E)-3-ethyl-3-4-(3-hydroxy-4,4-dimethyl-pentyl)-3-methyl-phenyl]-pent-1-enyl}-2-hydroxymethyl-phenyl)-methanol;
128. (4-{(E)-3-ethyl-3-[3-ethyl-4-(3-hydroxy-4,4-dimethyl-pentyl)-phenyl]-pent-1-enyl}-2-hydroxymethyl-phenyl)-methanol;
129. (E)-1-{4-[(E)-3-(3,4-bis-hydroxymethyl-phenyl)-1,1-diethyl-allyl]-2-methyl-phenyl}-4,4-dimethyl-pent-1-en-3-ol;
130. (E)-1-{4-[(E)-3-(3,4-bis-hydroxymethyl-phenyl)-1,1-diethyl-allyl]-2-methyl-phenyl}-4,4-dimethyl-pent-1-en-3-ol;
131. (4-{3-[3-ethyl-4-(3,3,3-trifluoro-2-hydroxy-propoxy)-phenyl]-3-methyl-butyl}-2-hydroxymethyl-phenyl)-methanol;
132. (4-{3-[3-ethyl-4-(3,3,3-trifluoro-2-hydroxy-propylsulphanyl)-phenyl]-3-methyl-butyl}-2-hydroxymethyl-phenyl)-methanol;

133. (4-{3-[3-ethyl-4-(4,4,4-trifluoro-3-hydroxy-butyl)-phenyl]-3-methyl-butyl}-2-hydroxymethyl-phenyl)-methanol;
134. (4-{3-[3-ethyl-4-((E)-4,4,4-trifluoro-3-hydroxy-but-1-enyl)-phenyl]-3-methyl-butyl}-2-hydroxymethyl-phenyl)-methanol;
135. (4-{3-[3-ethyl-4-(4,4,4-trifluoro-2-hydroxy-3-trifluoromethyl-butoxy)-phenyl]-3-methyl-butyl}-2-hydroxymethyl-phenyl)-methanol;
136. (4-{3-[3-ethyl-4-(4,4,4-trifluoro-2-hydroxy-3-trifluromethyl-butysulphenyl)-phenyl]-3-methyl-butyl}-2-hydroxymethyl-phenyl)-methanol;
137. (4-{[ethyl-(5,5,5-trifluoro-3-hydroxy-4-trifluoromethyl-pentyl)-phenyl]-methyl-butyl}-2-hydroxymethyl-phenyl)-methanol;
138. (E)-{4-[3-(3,4,bis-hydroxymethyl-phenyl)-1,1-dimethyl-propyl]-2-ethyl-phenyl}-5,5,5-trifluoro-4-trifluoromethyl-pent-1-en-ol;
139. (4-{3-ethyl-3-[3-ethyl-4-(3,3,3-trifluoro-2-hydroxy-propoxy)-phenyl]-pentyl}-2-hydroxymethyl-phenyl)-methanol;
140. (4-{3-ethyl-3-[3-ethyl-4-(3,3,3-trifluoro-2-hydroxy-propylsulphanyl)-phenyl]-pentyl}-2-hydroxymethyl-phenyl)-methanol;
141. (4-{3-ethyl-3-[3-ethyl-4-(4,4,4-trifluoro-3-hydroxy-butyl)-phenyl]-pentyl}-2-hydroxymethyl-phenyl)-methanol;
142. (4-{3-ethyl-3-[3-ethyl-4((E)-4,4,4-trifluoro-3-hydroxy-but-1-enyl)-phenyl]-pentyl}-2-hydroxymethyl-phenyl)-methanol;
143. (4-{3-ethyl-3-[3-ethyl-4-(4,4,4-trifluoro-2-hydroxy-3-trifluoromethyl-butoxy)-phenyl]-pentyl}-2-hydroxymethyl-phenyl)-methanol;
144. (4-{3-ethyl-3-[3-ethyl-4-(4,4,4-trifluoro-2-hydroxy-3-trifluoromethyl-butylsulphanyl)-phenyl]-pentyl}-2-hydroxymethyl-phenyl)-methanol;
145. (4-{ethyl-[ethyl-(5,5,5-trifluoro-3-hydroxy-4-trifluoromethyl-pentyl)-phenyl]-pentyl}-2-hydroxymethyl-phefiyl)-methanol;
146. (E)-{4-[3-(3,4-bis-hydroxymethyl-phenyl)-1,1-diethyl-propyl]-2-ethyl-phenyl}-5,5,5-trifluoro-4-trifluoromethyl-pent-1-en-3-ol
147. [4-(2-{1-[3-ethyl-4-(3,3,3-trifluoro-2-hydroxy-propoxy)-phenyl]-cyclohexyl}-ethyl)-2-hydroxymethyl-phenyl]-methanol;
148. [4-(2-{1-[3-ethyl-4-(3,3,3-trifluoro-2-hydroxy-propylsulphanyl)-phenyl]-cyclohexyl}-ethyl)-2-hydroxymethyl-phenyl]-methanol;
149. [4-(2-{1-[3-ethyl-4-(4,4,4-trifluoro-3-hydroxy-butyl)-phenyl]-cyclohexyl}-ethyl)-2-hydroxymethyl-phenyl]-methanol;
150. [4-(2-{1-[3-ethyl-4-((E)-4,4,4-trifluoro-3-hydroxy-but-1-enyl)-phenyl]-cyclohexyl}-ethyl)-2-hydroxymethyl-phenyl]-methanol;
151. [4-(2-{1-[3-ethyl-4-(4,4,4-trifluoro-2-hydroxy-3-trifluoromethyl-butoxy)-phenyl]-cyclohexyl}-ethyl)-2-hydroxymethyl-phenyl]-methanol;
152. [4-(2-{1-[3-ethyl-4-(4,4,4-trifluoro-2-hydroxy-3-trifluoromethyl-butylsulphanyl)-phenyl]-cyclohexyl}-ethyl)-2-hydroxymethyl-phenyl]-methanol;
153. [4-(2-{1-[ethyl-(5,5,5-trifluoro-3-hydroxy-4-trifluoromethyl-pentyl)-phenyl]-cyclohexyl}-ethyl)-2-hydroxymethyl-phenyl]-methanol;
154. (E)-[4-(1-[2-(3,4-bis-hydroxymethyl-phenyl)-ethyl]-cyclohexyl}-2-ethyl-phenyl)-5,5,5-trifluoro-4-trifluoromethyl-pent-1-en-3-ol;
155. (4-{2-ethyl-2-[3-ethyl-4-(3,3,3-trifluoro-2-hydroxy-propoxy)-phenyl]-butoxy}-2-hydroxymethyl-phenyl-methanol;
156. (4-{2-ethyl-2-[3-ethyl-4-(3,3,3-trifluoro-2-hydroxy-propylsulphanyl)-phenyl]-butoxy}-2-hydroxymethyl-phenyl)-methanol;
157. (4-{2-ethyl-2-[3-ethyl-4-(4,4,4-trifluoro-3-hydroxy-butyl)-phenyl]-butoxy}-2-hydroxymethyl-phenyl)-methanol;
158. (4-{2-ethyl-2-[3-ethyl-4-((E)-4,4,4-trifluoro-3-hydroxy-but-1-enyl)-phenyl]-butoxy}-2-hydroxymethyl-phenyl)-methanol;
159. (4-{2-ethyl-2-[3-ethyl-4-(4,4,4-trifluoro-2-hydroxy-3-trifluoromethyl-butoxy)-phenyl]-butoxy}-2-hydroxymethyl-phenyl)-methanol;
160. (4-{2-ethyl-2-[3-ethyl-4-(4,4,4-trifluoro-2-hydroxy-3-trifluoromethy-butylsulphanyl)-phenyl]-butoxy}-2-hydroxymethyl-phenyl)-methanol;
161. (4-{ethyl-[ethyl-(5,5,5-trifluoro-3-hydroxy-4-trifluoromethyl-pentyl)-phenyl]-butoxy}-2-hydroxymethyl-phenyl)-methanol;
162. (E)-{4-[1-(3,4-bis-hydroxymethyl-phenoxymethyl)-1-ethyl-propyl]-2-ethyl-phenyl}-5,5,5-trifluoro-4-trifluoromethyl-pent-1-en-3-ol.

The above compounds may also be used in the form of a mixture.

The compounds of general formula (I) may be prepared via the following synthesis scheme shown in the Figure of Drawing.

The compound 2 may be prepared from the compound 1 by selective bromination, followed by protection (P) of the phenol functional group. The compounds having the structure 3 may be obtained from the compounds 2 by Stille type coupling with an appropriate organotin partner, for example an allyltributyltin or a cyanomethyltributyltin.

The compounds having the structure 4 may be obtained from 3a:

in the case where B-T is $CH_2$—$CH_2$, by hydroboration of the olefin functional group, followed by Suzuki type coupling with a triflate partner of the dimethyl 4-trifluoromethanesulphonyloxyphthalate type, in the case where B-T is CH═CH, after ozonolysis of the olefin, followed by a Wittig on Horner-Emmons type reaction with for example a phosphorus-containing partner of the dimethyl 4-(diethoxyphosphorylmethyl)phthalate type, in the case where B-T is $CH_2$—O, $CH_2$—S or $CH_2$—NH—, after reductive ozonolysis of the olefin functional group, followed by a Mitsunobu type reaction with a phenol or thiophenol or aniline partner of the dimethyl 4-hydroxy (or mercapto or amino)phthalate type, followed by deprotection of the phenol functional group.

The compounds having the structure 5 may then be obtained in the following manner: the phenol functional group may be substituted with an α-bromoketone. Next, the compounds obtained may be reduced to the final compounds 5 ($R_2$=H) by addition of hydrides, such as lithium aluminum hydride for example, or alternatively the ketones may be alkylated with selective reagents such as organozinc reagents, and then the ester functional groups may be reduced with hydrides, in order to obtain the final compounds 5 ($R_2$ different from H).

The compounds having the structure 6 may be obtained from the compounds of the 3b type, by double alkylation of the benzyl position, for example in the presence of an alkyl halide $R_4$—X and of lithium diisopropylamide, followed by reduction of the nitrile functional group to an aldehyde.

The compounds having the structure 7 may then be obtained from 6:

in the case where B-T is CH=CH, after a Wittig or Horner-Emmons type reaction with for example a phosphorus-containing partner of the dimethyl 4-(diethoxyphosphorylmethyl)phthalate type, in the case where B-T is $CH_2$—$CH_2$, by hydrogenation of the olefin functional group obtained from B-T=CH=CH, and finally in the case where B-T is $CH_2$—O, $CH_2$—S or $CH_2$—NH, after reduction of the aldehyde functional group to an alcohol followed by a Mitsunobu type reaction with a phenol or thiophenol or aniline partner of the dimethyl 4-hydroxy(or mercapto or amino)phthalate type, followed by deprotection of the phenol functional group.

The compounds having the structure 8 may then be obtained in the following manner: the phenol functional group may be substituted with an α-bromoketone. Next, the compounds obtained may be reduced to the final compounds 8 ($R_2$=H) by addition of hydrides, such as lithium aluminum hydride for example, or alternatively the ketones may be alkylated with selective reagents such as organozinc reagents, and then the ester functional groups may be reduced with hydrides, in order to obtain the final compounds 8 ($R_2$ different from H).

The compounds having the structure 9 may be obtained after conversion to a trifluoromethanesulphonate of the phenol functional group of the compounds of type 7:

when Q-A is CH=CH, the intermediate thus obtained may be converted after a Heck type reaction with a corresponding vinyl ketone of the $CH_2$=$CHC(O)R_1$ type, when Q-A is $CH_2$—CH, the compounds may then be obtained after hydrogenation of the olefin functional group of the compounds 9 with Q-A=CH=CH, when Q-A is ethynyl, the compounds are obtained after a Sonogashira type coupling between a true alkyne functional group and the trifluoromethanesulphonate derived from 7 described above.

The compounds 9 obtained may be reduced to the final compounds 10 ($R_2$=H) by addition of hydrides, such as lithium aluminum hydride for example, or alternatively the ketones may be alkylated with selective reagents such as organozinc reagents, and then the ester functional groups may be reduced with hydrides, in order to obtain the final compounds 10 ($R_2$ different from H).

The compounds of general formula (I) exhibit biological properties similar to those of vitamin D, in particular the vitamin D response element (VDRE) transactivating properties, such as an agonist or antagonist activity towards receptors for vitamin D or its derivatives. Vitamins D or their derivatives are understood to mean, for example, the derivatives of vitamin $D_2$ or $D_3$ and in particular 1,25-dihydroxy vitamin $D_3$ (calcitriol).

This agonist activity towards receptors for vitamin D or its derivatives may be demonstrated in vitro by methods recognized in the field of the study of gene transcription (Hansen et al., *The Society for Investigative Dermatology*, Vol. 1, No. 1, April 1996).

The biological properties analogous to vitamin D may also be measured by the capacity of the product to induce differentiation of promyelocytic leukaemia cells HL60. The protocol and the results obtained with the compounds according to the invention are described in Example 6 of the present application.

By way of example, the VDR agonist activity may be tested on the HeLa cell line, by co-transfecting a human VDR receptor expression vector and the reporter plasmid p240Hase-CAT. The agonist activity may also be characterized in this co-transfection system by the determination of the dose necessary to reach 50% of the maximum activity of the product (AC50). The detail of the protocol for this test and the results obtained with the compounds according to the invention are described in Example 7 of the present application.

The biological properties which are similar to vitamin D may also be measured by the capacity of the product to inhibit the proliferation of normal human keratinocytes (NHK in culture). The product is added to NHKs cultured under conditions promoting the proliferative state. The product is left in contact with the cells for 5 days. The number of proliferative cells is measured by incorporation of bromodeoxyuridine (BRdU) into DNA. The protocol for this test and the results obtained with the compounds according to the invention are described in Example 8 of the present application.

The present invention also features medicaments comprising the subject compounds described above.

The compounds according to the invention are particularly useful in the following fields of treatment:

1) for treating dermatological conditions or afflictions linked to a keratinocyte or sebocyte differentiation or proliferation disorder, in particular for treating acne vulgaris, comedo-type acne, polymorphic acne, acne rosacea, nodulocystic acne, acne conglobata, senile acne, secondary acne such as solar acne, acne medicamentosa or occupational acne;

2) for treating other types of keratinization disorders, in particular ichthyosis, ichthyosiform states, Darier's disease, keratosis palmaris et plantaris, leukoplasia, leukoplasiform states, cutaneous or mucosal (buccal) lichen;

3) for treating other dermatological conditions or afflictions linked to a keratinization disorder with an inflammatory and/or immunoallergic component, and in particular all the forms of psoriasis, whether cutaneous, mucosal or ungula, and even psoriatic rheumatism or cutaneous atopy, such as eczema or respiratory atopy or gingival hypertrophy;

4) for treating certain cutaneous inflammatory conditions or afflictions which do not exhibit keratinization disorders, such as atopic eczema and contact allergies;

5) for treating any dermal or epidermal proliferations whether benign or malignant, whether of viral origin or not, such as verruca vulgaris, verruca plana and epidermodysplasia verruciformis, oral or florid papillomatoses and proliferations which may be induced by ultraviolet radiation in particular in the case of baso- and spinocelular epithelioma;

6) for treating other dermatological disorders such as bullous dermatoses and collagen diseases;

7) for preventing or treating skin aging, whether photo-induced or chronologic, or for reducing pigmentations and actinic keratoses, or any cutaneous pathologies associated with chronologic or actinic aging;

8) for preventing or treating cicatrization disorders or for preventing or repairing stretch marks;

9) for combating disorders of the sebaceous function, such as hyperseborrhoea of acne or simple seborrhoea or seborrheic eczema;

10) for treating certain ophthalmological disorders, in particular corneopathies;

11) in the treatment or prevention of cancerous or pre-cancerous states of cutaneous or non-cutaneous cancers exhibiting or capable of being induced so as to exhibit vitamin D receptors, such as, but without limitation, breast cancer, leukaemia, myelodysplasic syndromes and lymphomas, carcinomas of the cells of the Malpighian epithelium and gastrointestinal cancers, melanomas and osteosarcoma;

12) in the treatment of inflammatory conditions or afflictions such as arthritis or rheumatoid arthritis;

13) in the treatment of any condition or affliction of viral origin at the cutaneous level or in general;

14) in the prevention or treatment of alopecia of various origins, in particular alopecia due to chemotherapy, or to radiation;

15) in the treatment of dermatological or general conditions or afflictions with an immunological component;

16) in the treatment of immunological conditions or afflictions such as autoimmune diseases (such as, but without limitation, type 1 diabetes mellitus, multiple sclerosis, lupus and lupus-type conditions, asthma, glomerulonephritis and the like), selective dysfunctions of the immune system (for example AIDS) and the prevention of immune rejection such as the rejection of grafts (for example the kidney, heart, bone marrow, liver, pancreatic islets or the whole pancreas, the skin and the like) or the prevention of graft-versus-host disease;

17) in the treatment of endocrinal conditions or afflictions which can be treated with vitamin D analogues such as those advantageously modulating hormonal secretion such as by increasing the secretion of insulin or selectively suppressing the secretion of the parathyroid hormone (for example in chronic renal insufficiency and secondary hyperparathyroidism);

18) in the treatment of conditions or afflictions characterized by an abnormal management of intracellular calcium; and 19) in the treatment and/or prevention of vitamin D deficiencies and of other conditions or afflictions of the homeostasis of the minerals in the plasma and the bones, such as rickets, osteomalacia, osteoporosis, in particular in the case of menopausal women, renal osteodystrophy, parathyroid function disorders.

The present invention also features pharmaceutical compositions comprising at least one compound as defined above, formulated into a pharmaceutically acceptable carrier therefor.

The administration of the compounds according to the invention may be via the enteral, parenteral, topical or ocular route.

By the enteral route, the pharmaceutical compositions may be provided in the form of tablets, gelatin capsules, sugar-coated tablets, syrups, suspensions, solutions, powders, granules, emulsions, lipid or polymeric microspheres or nanospheres or vesicles which permit a controlled release.

By the parenteral route, the compositions may be provided in the form of solutions or suspensions for infusion or for injection.

The compounds according to the invention are generally administered at a daily dose of about 0.001 µg/kg to 1000 µg/kg and preferably about 0.01 µg/kg to 100 µg/kg as bodyweight, in a regime or regimen of 1 to 3 doses.

By the topical route, the pharmaceutical compositions based on compounds according to the invention are useful for the treatment of the skin, the scalp and the mucous membranes and are provided in the form of salves, creams, milks, ointments, powders, impregnated pads, solutions, gels, sprays, lotions or suspensions. They may also be provided in the form of lipid or polymeric microspheres or nanospheres or vesicles or of polymeric patches and hydrogels allowing a controlled release. These compositions for the topical route may be provided either in anhydrous form or in an aqueous form, depending on the clinical indication.

By the ocular route, they are mainly collyria.

The compositions for topical or ocular administration contain at least one compound according to the invention at a concentration preferably from 0.0001% to 5% and more preferably from 0.001% to 1% by weight relative to the total weight of the composition.

The compounds according to the invention also find application in the cosmetics field, in particular in body and hair care and in particular for the treatment of skins with a tendency towards acne, for hair regrowth, against hair loss, for combating the greasy appearance of the skin or the hair, in protecting against the harmful effects of the sun and in the treatment of dry skins, for preventing and/or for treating photoinduced or chronologic aging.

The present invention therefore also features cosmetic compositions containing, in a cosmetically acceptable carrier, at least one compound as defined above.

This cosmetic composition may be provided, in particular, in the form of a cream, a milk, a lotion, a gel, a suspension of lipid or polymeric microspheres or nanospheres or vesicles, a soap or a shampoo.

The concentration of compound of general formula (I) in the cosmetic compositions according to the invention advantageously ranges from 0.001% to 3% by weight relative to the total weight of the composition.

In the pharmaceutical and cosmetic fields, the compounds according to the invention may be advantageously formulated in combination with inert or even pharmacodynamically or cosmetically active additives or combinations of these additives and, in particular:

wetting agents;
taste-enhancing agents;
preservatives such as para-hydroxybenzoic acid esters;
stabilizing agents;
moisture-regulating agents;
pH-regulating agents;
osmotic pressure-modifying agents;
emulsifying agents;
UV-A and UV-B screening agents;
antioxidants such as α-tocopherol, butylated hydroxyanisole, butylated hydroxytoluene, Super Oxide Dismutase, Ubiquinol or certain metal chelators;
depigmenting agents such as hydroquinone, azelaic acid, caffeic acid or kojic acid;
emollients;
moisturizing agents such as glycerol, PEG 400, thiamorpholinone and its derivatives, or urea;
anti-seborrhoeic or anti-acne agents, such as S-carboxymethylcysteine, S-benzylcysteamine, their salts and their derivatives, or benzoyl peroxide;
antibiotics such as erythromycin and its esters, neomycin, clindamycin and its esters, tetracyclins;
anti-fungal agents such as ketoconazole or 4,5-polymethylene-3-isothiazolinones;
agents which limit hair loss, such as Minoxidil (2,4-diamino-6-piperidinopyrimidine 3-oxide) and its derivatives, Diazoxicle (7-chloro-3-methyl-1,2,4-benzothiadiazine 1,1-dioxide) and Phenytoin (5,4-diphenyl-2,4-imidazolidinedione);
nonsteroidal anti-inflammatory agents;
carotenoides, and in particular β-carotene;
anti-psoriatic agents such as anthralin and its derivatives;
5,8,11,14-eicosatetraynoic and 5,8,11-eicosatrynoic acids, their esters and amides;
retinoids, namely, ligands for the RAR or RXR receptors, which may be natural or synthetic;
corticosteroids or oestrogens;

α-hydroxy acids and α-keto acids or their derivatives, such as lactic, malic, citric, glycolic, mandelic, tartaric, glyceric and ascorbic acids, and their salts, amides or esters, or β-hydroxy acids or their derivatives, such as salicylic acid and its salts, amides or esters;

ion channel, such as potassium channel, blockers;

or alternatively, more particularly for pharmaceutical compositions, in combination with medicaments known to interfere with the immune system (for example cyclosporin, FK 506, glucocorticoids, monoclonal antibodies, cytokines or growth factors, and the like).

Of course, one skilled in this art will be careful to choose the possible compound(s) to be added to these compositions such that the advantageous properties of the compounds of the present invention are not or not substantially impaired by the addition envisaged.

The present invention also features cosmetic compositions as defined above for body or hair hygiene.

It also features a cosmetic regime or regimen of a cosmetic composition as defined for preventing and/or treating photoinduced or chronologic skin aging.

In order to further illustrate the present invention and the advantages thereof, the following specific examples are given, of specific compounds and formulations and tests for evaluating the biological activity thereof, it being understood that same are intended only as illustrative and in nowise limitative. In said examples to follow, all parts and percentages are given by weight, unless otherwise indicated.

EXAMPLE 1

Synthesis of 1-{4-[3-(3,4-Bis-hydroxymethyl-phenyl)-propyl]-2-ethyl-phenoxy}-3,3-dimethyl-butan-2-ol a. Preparation of 4-Bromo-2-ethylphenol 15 g (123 mmol) of 2-ethylphenol are dissolved in 150 ml of chloroform. 59 g (123 mmol) of tetrabutylammonium tribromide are added in portions of 10 g, and the reaction medium is stirred for 20 minutes. The medium is then poured into a saturated sodium thiosulphate solution, and then the pH is adjusted to 7. The mixture is extracted with dichloromethane. After drying and concentration, the residue obtained is purified by chromatography on a silica column (eluent ethyl acetate 10/heptane 90). A yellow oil is obtained (m=24.5 g, y=99%).

b. Preparation of 4-Bromo-1-ethoxymethoxy-2-ethylbenzene 24.5 g (121 mmol) of 4-bromo-2-ethylphenol are dissolved in 150 ml of DMF, and this solution is slowly added to a suspension of 5.3 g (133 mmol) of sodium hydride in 50 ml of DMF. The medium is stirred for 30 minutes, and then 12.4 ml (133 mmol) of ethoxymethyl chloride are added. The reaction medium is stirred for 4 hours at room temperature, and then poured into water and extracted with ethyl acetate. The organic phases are washed with water, and the residue obtained after drying and concentration is purified by chromatography on a silica column (eluent ethyl acetate 10/heptane 90). A yellow oil is obtained (m=25 g, y=80%)

c. Preparation of 4-Allyl-1-ethoxymethoxy-2-ethylbenzene 15 g (58 mmol) of 4-bromo-1-ethoxymethoxy-2-ethylbenzene are dissolved in 150 ml of DMF. 26.9 ml (87 mmol) of allyltributyltin are added, and then the mixture is degassed with a nitrogen stream. 1.2 g (1.8 mmol) of dichlorobis (triphenylphosphino)palladium are added, and the medium is heated at 120° C. for 10 hours. The reaction medium is poured into water, and then extracted with ethyl acetate. The residue obtained after drying and concentration is purified by chromatography on a silica column (eluent heptane, and then heptane 95/ethyl acetate 5). A yellow oil is obtained (m=13.6 g, y=100%).

d. Preparation of Dimethyl 4-trifluoromethanesulphonyloxyphthalate 21 g (100 mmol) of dimethyl 4-hydroxyphthalate are dissolved in 500 ml of dichloromethane. The reaction medium is cooled to 0° C., and 21 ml (155 mmol) of triethylamine are added. 30 g (105 mmol) of triflic anhydride are slowly added, and the reaction medium is slowly brought to room temperature, and is then treated with water, and extracted with dichloromethane. The organic phases are washed with a dilute sodium bicarbonate solution, and then dried and concentrated. The residue is purified by chromatography on a silica column (eluent ethyl acetate 30/heptane 70). A yellow oil is obtained (m=27 g, y=79%).

e. Preparation of Dimethyl 4-[3-(4-ethoxymethoxy-3-ethylphenyl)propyl]phthalate 5 g (22.7 mmol) of 4-allyl-1-ethoxymethoxy-2-ethylbenzene are dissolved in 100 ml of anhydrous THF, and the medium is cooled to 0° C. 6.6 g (27 mmol) of 9-BBN are added, and the medium is brought to room temperature and then stirred for 12 hours. A solution of 7.8 g (22.6 mmol) of dimethyl 4-trifluoromethanesulphonyloxyphthalate in 100 ml of DMF is added, as well as 6.2 g (44.8 mmol) of potassium carbonate. The reaction medium is degassed with a nitrogen stream, and then 930 mg (1.1 mmol) of dichloropalladium diphosphinoferrocene are added. The medium is heated at 50° C. for 3 hours, and then poured into an ammonium chloride solution and extracted with ethyl acetate. The residue obtained after drying and concentration is purified by chromatography on a silica column (eluent heptane, and then heptane 85/ethyl acetate 15). A yellow oil is obtained (m=6.9 g, y=73%).

f. Preparation of Dimethyl 4-[3-(3-ethyl-4-hydroxyphenyl)propyl]phthalate 6.9 g (16.6 mmol) of dimethyl 4-[3-(4-ethoxymethoxy-3-ethylphenyl)propyl]phthalate are dissolved in 100 ml of methanol. 3 ml of concentrated sulphuric acid are added dropwise, and the medium is stirred fro 1 hour, and then poured into water, and extracted with dichloromethane. The organic phases are dried and concentrated. The residue obtained is purified by chromatography on a silica column (eluent heptane 80/ethyl acetate 20). A colorless oil is obtained (m=5 g, y=84%).

g. Preparation of Dimethyl 4-[3-[4-(3,3-dimethyl-2-oxobutoxy)-3-ethylphenyl]propyl}phthalate 800 mg (2.2 mmol) of dimethyl 4-[3-(3-ethyl-4-hydroxyphenyl)propyl}phthalate are dissolved in 40 ml of 2-butanone. 340 mg (2.5 mmol) of potassium carbonate and 330 μl (2.5 mmol) of 1-bromopinacolone are added. The reaction medium is heated under reflux for 8 hours, and is then filtered on celite. The residue obtained is purified by chromatography on a silica column (eluent ethyl acetate 20/heptane 80). A colorless oil is obtained (m=920 mg; y=90%).

h. Synthesis of 1-{4-[3-(3,4-Bis-hydroxymethyl-phenyl)-propyl]-2-ethyl-phenoxy}-3,3-dimethyl-butan-2-ol 900 mg (2 mmol) of dimethyl 4-{3-[4-(3,3-dimethyl-2-oxobutoxy)-3-ethylphenyl]propyl}phthalate are dissolved in 20 ml of THF, and slowly added to a suspension of 375 mg (10 mmol) of lithium aluminum hydride. The reaction medium is stirred for 30 minutes at room temperature, and is then sequentially treated by slow addition of 400 µl of water, 400 µl of 15% sodium hydroxide and 1 ml of water. The reaction medium is poured into a 1% hydrochloric acid solution, and then extracted with ethyl ether. The residue obtained after drying and concentrating is purified by chromatography on a silica column. A thick colorless oil is obtained (m=760 mg, y=95%).

$^1$H NMR (CDCl$_3$): 1.01 (s, 9H); 1.19 (t, J=7.4 Hz, 3H); 1.92 (m, 2H); 2.0 (bs, 3H); 2.56-2.66 (m, 6H); 3.71 (dd, J1=2.5 Hz, J2=8.7 Hz, 1H); 3.86 (t, 1H, J=8.7 Hz); 4.09 (dd, J1=8.7 H, J2=2.5 Hz, 1H); 4.73 (s, 4H), 6.75 (d, J=8 Hz, 1H); 6.94-6.97 (m, 2H); 7.14 (d, J=7.6 Hz, 1H); 7.19 (s, 1H); 7.28 (s, 1H).

EXAMPLE 2

Synthesis of 1-{4-[3-(3,4-Bis-hydroxymethyl-phenyl)-propyl]-2-methyl-phenoxy}-3,3-dimethyl-butan-2-ol a. Preparation of 4-Bromo-2-methylphenol

In a manner similar to Example 1a, by reacting 10 g (91 mmol) of 2-methylphenol with 44 g (91 mmol) of tetrabutylammonium tribromicie. A yellow oil is obtained (m=16.3 g, y=95%).

b. Preparation of 4-Bromo-1-methoxymethoxy-2-ethylbenzene

In a manner similar to Example 1b, by reacting 15 g (79 mmol) of 4-bromo-2-methylphenol with 3.5 g (87 mmol) of sodium hydride and 8.1 ml (87 mmol) of ethoxymethyl chloride. A yellow oil is obtained (m=16.4 g, y=84%).

c. Preparation of 4-Allyl-1-ethoxymethoxy-2-methylbenzene

In a manner similar to Example 1c, by reacting 16 g (65 mmol) of 4-bromo-1-ethoxymethoxy-2-methylbenzene with 30 ml (97 mmol) of allyltributyltin and 1.35 g (2 mmol) of dichlorobis (triphenylphosphino)palladium. A yellow oil is obtained (m=12:1 g, y=89%).

d. Preparation of Dimethyl 4-[3-(4-methoxymethoxy-3-methylphenyl)propyl]phthalate In a manner similar to Example 1e, by reacting 4.5 g (21.6 mmol) of 4-allyl-1-ethoxymethoxy-2-methylbenzene with 6.3 g (25.7 mmol) of 9-BBN, 7.4 g (21.6 mmol) of dimethyl 4-trifluoromethanesulphonyloxyphthalate, 5.9 g (42.6 mmol) of potassium carbonate and 880 mg (1.05 mmol) of dichloropalladium diphosphinoferrocene. A yellow oil is obtained (m=7 g, y=80%).

e. Preparation of Dimethyl 4-[3-(3-methyl-4-hydroxyphenyl)propyl]phthalate

In a manner similar to Example 1f, by reacting 6.9 g (17.2 mmol) of dimethyl 4-[3-(4-ethoxymethoxy-3-methylphenyl)propyl]phthalate in 100 ml of methanol with 3 ml of concentrated sulphuric acid. A colorless oil is obtained (m=5.2 g; y=88%).

f. Preparation of Dimethyl 4-{3-[4-(3,3-dimethyl-2-oxobutoxy)-3-methylphenyl]propyl}phthalate In a manner similar to Example 1g, by reacting 900 mg (2.6 mmol) of dimethyl 4-[3-(3-methyl-4-hydroxyphenyl)propyl]phthalate with 400 mg (2.9 mmol) of potassium carbonate and 390 µl (2.9 mmol) of 1-bromopinacolone. A colorless oil is obtained (m=910 mg; y=79%).

g. Synthesis of 1-{4-[3-(3,4-Bis-hydroxymethyl-phenyl)-propyl]-2-methyl-phenoxy}-3,3-dimethyl-butan-2-ol In a manner similar to Example 1h, by reacting 900 mg (2.1 mmol) of dimethyl 4-{3-[4-(3,3-dimethyl-2-oxobutoxy)-3-methylphenyl]propyl}phthalate with 375 mg (10 mmol) of lithium aluminum hydride. A thick colorless oil is obtained (m=780 mg, y=96%).

$^1$H NMR (DMSO): 0.78 (s, 9H); 1.65-1.72 (m, 2H); 2.0 (s, 3H); 2.32-2.44 (m, 4H); 3.30 (m, 1H); 3.61 (dd, 1H, J1=8.4 Hz, J2=2.3 Hz); 3.86 (dd, J1=8.4 H, J2=2.3 Hz, 1H); 4.36 (t, J=6 Hz, 4H), 4.64 (d, J=5.3 Hz, 1H); 4.82-4.91 (m, 2H); 6.68 (d, J=8 Hz, 1H); 6.78-6.91 (m, 3H); 7.06-7.14 (m, 2H).

EXAMPLE 3

Synthesis of (4-{3-(3-Ethyl-4-(2-ethyl-2-hydroxy-butoxy)-phenyl]-propyl}-2-hydroxymethyl-phenyl)-methanol a. Preparation of 4-[3-(3,4-Bis-hydroxymethyl-phenyl)-propyl]-2-ethyl-phenol 1.7 g (4.8 mmol) of dimethyl 4-[3-(3-ethyl-4-hydroxyphenyl)propyl]phthalate (Example 1f are dissolved in 50 ml of ethyl ether, and this solution is slowly added to a suspension of 435 mg (11.4 mmol) of lithium aluminum hydride. The medium is stirred for 30 minutes and is then sequentially treated with 450 µl of water, 450 µl of 15% sodium hydroxide and 1.5 ml of water. The reaction medium is poured into a 1N hydrochloric acid solution, and extracted with ethyl ether. A white solid is obtained (m=1.2 g, m.p.=82° C., y=84%).

b. Preparation of Ethyl {4-[3-(3,4-bis-hydroxymethyl-phenyl)-propyl]-2-ethyl-phenoxyl-acetate In a manner similar to Example 1g, by reacting 1.1 g (3.7 mmol) of 4-[3-(3,4-bis-hydroxymethyl-phenyl)-propyl]-2-ethyl-phenol with 560 mg (4 mmol) of potassium carbonate and 450 µl of ethyl bromoacetate. A colorless oil is obtained (m=680 mg, y=48%).

c. Synthesis of (4-{3-[3-Ethyl-4-(2-ethyl-2-hydroxy-butoxy)-phenyl]propyl]-2-hydroxymethyl-phenyl)-methanol 640 mg (1.65 mmol) of ethyl {4-[3-(3,4-bis-hydroxymethyl-phenyl)-propyl]-2-ethyl-phenoxy}-acetate are dissolved in 30 ml of THF. 2.2 ml (6.6 mmol) of a 3M ethylmagnesium bromide solution are added dropwise. The reaction medium is stirred for 30 minutes, and is then treated with a saturated ammonium chloride solution. The residue obtained after extraction and concentration is purified by chromatography on a silica column. A colorless oil is obtained (m=510 mg, y=77%).

$^1$H NMR (CDCl$_3$): 0.94 (t, J=7.6 Hz, 6H); 1.19 (t, J=7.4 Hz, 3H); 1.67 (q, J=7.6 Hz, 4H); 1.92 (m, 2H); 2.15 (bs, 3H); 2.56-2.66 (m, 6H); 3.80 (s, 2H); 4.72 (s, 4H); 6.75 (d, J=8 Hz, 1H); 6.94-6.96 (m, 2H); 7.13 (d, J=7.6 Hz, 1H); 7.18 (s, 1H); 7.27 (s, 1H).

EXAMPLE 4

Synthesis of (4-{3-(4-(2-Ethyl-2-hydroxy-butoxy)-3-methyl-phenyl]-propyl)-2-hydroxymethyl-phenyl)-methanol a. Preparation of 4-[3-(3,4-Bis-hydroxymethyl-phenyl)-propyl]-2-methyl-phenol In a manner similar to Example 3a, by reacting 1 g (2.9 mmol) of dimethyl 4-[3-(3-methyl-4-hydroxyphenyl)propyl]phthalate (Example 2e) with 260 mg (7 mmol) of lithium aluminum hydride. A white solid is obtained (m=740 mg, m.p.=92° C., y=89%).

b. Preparation of Ethyl {4-[3-(3,4-bis-hydroxymethyl-phenyl)-propyl]-2-methyl-phenoxy]-acetate In a manner similar to Example 3b, by reacting 720 mg (2.5 mmol) with 380 mg (2.7 mmol) of potassium carbonate and 310 µl (2.7 mmol) of ethyl bromoacetate. A colorless oil is obtained (m=540 mg, y=58%).

c. Synthesis of (4-{3-[4-(2-Ethyl-2-hydroxy-butoxy)-3-methyl-phenyl]-propyl}-2-hydroxymethyl-phenyl)-methanol In a manner similar to Example 3c, reacting 530 mg (1.42 mmol) of ethyl {4-[3-(3,4-bis-hydroxymethyl-phenyl)-propyl]-2-methyl-phenoxy}-acetate with 2.4 ml (7 mmol) of a 3M ethylmagnesium bromide solution. A colorless oil is obtained (m=410 mg y=75%).

$^1$H NMR (DMSO): 0.64 (t, J=7.6 Hz, 6H); 1.33 (q, J=7.4 Hz, 4H); 1.59-1.62 (m, 2H); 1.92 (s, 3H); 2.26-2.37 (m, 4H); 3.30 (m, 1H); 3.46 (s, SH); 4.08 (s, 1H); 4.27-4.31 (m, 4H), 4.77 (t, J=5.3 Hz, 1H); 4.82 (t, J=5.3 Hz, 1H); 6.58 (d, J=8 Hz, !H); 6.72-6.74 (m, 2H); 6.82-6.84 (m, 1H); 7.00 (s, 1H); 7.05 (d, J=7.7 Hz, 1H).

EXAMPLE 5

Formulations

1) Oral Route:
(a) The Following Composition is Formulated into a 0.2-g Tablet:

| | |
|---|---|
| Compound of Example 2 | 0.005 g |
| Pregelatinized starch | 0.065 g |
| Microcrystalline cellulose | 0.075 g |
| Lactose | 0.050 g |
| Magnesium stearate | 0.005 g |

For the treatment of ichthyosis, 1 to 3 tablets are administered to an adult individual per day for 1 to 12 months depending on the seriousness of the case treated.

(b) An oral Suspension to be Packaged in 5-ml Vials is Prepared:

| | |
|---|---|
| Compound of Example 3 | 0.050 mg |
| Glycerin | 0.500 g |
| Sorbitol at 70% | 0.500 g |
| Sodium saccharinate | 0.010 g |
| Methyl para-hydroxyberizoate | 0.040 g |
| Flavoring | qs |
| Purified water | qs 5 ml |

For the treatment of acne, 1 vial is administered to an adult individual per day for 1 to 12 months depending on the seriousness of the case treated.

(c) The Following Formulation to be Packaged in Gelatin Capsules is Prepared:

| | |
|---|---|
| Compound of Example 4 | 0.0001 mg |
| Maize starch | 0.060 g |
| Lactose | qs 0.300 g |

The gelatin capsules comprise gelatin, titanium oxide and a preservative.

In the treatment of psoriasis, 1 gelatin capsule is administered to an adult individual per day for 1 to 12 months.

(d) The Following Formulation to be Packaged in Gelatin Capsules is Prepared:

| | |
|---|---|
| Compound of Example 1 | 0.01 mg |
| Compound of Example 3 | 0.01 mg |
| Cyclosporin | 0.050 g |
| Maize starch | 0.060 g |
| Lactose | qs 0.300 g |

The gelatin capsules comprise gelatin, titanium oxide and a preservative.

In the treatment of psoriasis, 1 gelatin capsule is administered to an adult individual per day for 1 to 12 months.

2) Topical Route:
(a) The Following Nonionic Water-in-Oil Cream is Prepared:

| | |
|---|---|
| Compound of Example 3 | 0.100 g |
| Mixture of emulsive lanolin alcohols, of waxes and of refined oils, sold by Beiersdorf under the name "Eucérine anhydre" | 39.900 g |
| Methyl para-hydroxybenzoate | 0.075 g |
| Propyl para-hydroxybenzoate | 0.075 g |
| Sterile demineralized water | qs 100.000 g |

This cream is applied to a psotiatic skin once or twice per day for 1 to 12 months.

(b) A Gel is Prepared from the Following Formulation:

| | |
|---|---|
| Compound of Example 2 | 0.001 g |
| Erythromycin base | 4.000 g |
| Butylated hydroxytoluene | 0.050 g |
| Hydroxypropylcellulose sold by Hercules under the name "KLUCEL HF" | 2.000 g |
| Ethanol (at 95%) | qs 100.000 g |

This gel is applied to a skin affected by dermatosis or a skin with acne 1 to 3 times per day for 6 to 12 weeks depending on the seriousness pf the case treated.

(c) An Anti-Seborrhoeic Lotion is Prepared by Mixing the Following Ingredients:

| | |
|---|---|
| Compound of Example 1 | 0.030 g |
| Propylene glycol | 5.000 g |
| Butylated hydroxytoluene | 0.100 g |
| Ethanol (at 95%) | qs 100.000 g |

This lotion is applied twice per day to a seborrhoeic scalp and a significant improvement is observed within a period of between 2 and 6 weeks.

(d) A Cosmetic Composition Against the Harmful Effects of the Sun is Prepared by Mixing the Following Ingredients:

| | |
|---|---|
| Compound of Example 3 | 0.500 g |
| Compound of Example 4 | 0.500 g |
| Benzylidene camphor | 4.000 g |
| Fatty acid triglycerides | 31.000 g |
| Glycerol monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Perfume | 0.400 g |
| Demineralized water | qs 100.000 g |

This composition is applied daily; it combats photoinduced aging.

(e) The Following Oil-in-Water Cream is Prepared:

| | |
|---|---|
| Compound of Example 4 | 0.500 g |
| Retinoic acid | 0.020 g |
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100.000 g |

This cream is applied to a psoriatic skin once or twice per day for 30 days for intensive treatment and indefinitely for maintenance.

(f) A Topical Gel is Prepared from the Following Ingredients:

| | |
|---|---|
| Compound of Example 2 | 0.050 g |
| Ethanol | 43.000 g |
| α-Tocopherol | 0.050 g |
| Carboxyvinyl polymer sold under the name "Carbopol 941" by "Goodrich" | 0.500 g |
| Triethanolamine in aqueous solution at 20% by weight | 3.800 g |
| Water | 9.300 g |
| Propylene glycol. | qs 100.00 g |

This gel is applied in the treatment of acne 1 to 3 times per day for 6 to 12 weeks depending on the seriousness of the case treated.

(g) A Hair Lotion Against Hair Loss and for Regrowth is Prepared by Mixing the Following Ingredients:

| | |
|---|---|
| Compound of Example 4 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylated hydroxyanisole | 0.01 g |
| Butylated hydroxytoluene | 0.02 g |
| Water | qs 100.00 g |

This lotion is applied once or twice per day for 3 months to a scalp having suffered a loss indefinitely for maintenance treatment.

(h) An Anti-Acne Cream is Prepared by Mixing the Following Ingredients:

| | |
|---|---|
| Compound of Example 1 | 0.050 g |
| Retinoic acid | 0.010 g |
| Mixture of glycerol stearates and polyethylene glycol (75 mol) sold under the name "Gelot 64" by "GATTEFOSSE" | 15.000 g |
| Polyoxyethylenated stone oil containing 6 mol of ethylene oxide sold under the name "Labrafil M2130 CS" by "GATTEFOSSE" | 8.000 g |
| Perhydrosqualene | 10.000 g |
| Preservatives | qs |
| Polyethylene glycol (molecular mass = 400) | 8.000 g |
| Disodium salt of ethylenediamine-tetraacetic acid | 0.050 g |
| Purified water | qs 100.000 g |

This cream is applied to a skin affected by dermatosis or a skin with acne 1 to 3 times per day for 6 to 12 weeks.

(i) An Oil-in-Water Cream is Prepared from the Following Formulation:

| | |
|---|---|
| Compound of Example 2 | 0.020 g |
| Betamethasone 17-valerate | 0.050 g |
| S-carboxymethylcysteine | 3.000 g |
| Polyoxyethylene stearate (40 mol of ethylene oxide) sold under the name "Myrj 52" by "ATLAS" | 4.000 g |
| Sorbitan monolaurate, polyoxyethylene containing 20 mol of ethylene oxide sold under the name "Tween 20" by "ATLAS" | 1.800 g |
| Mixture of glycerol mono- and distearate sold under the name "Géléol" by "GATTEFOSSE" | 4.200 g |
| Propylene glycol | 10.000 g |
| Butylated hydroxyanisole | 0.010 g |
| Butylated hydroxytoluene | 0.020 g |
| Cetylstearyl alcohol | 6.200 g |
| Preservatives | qs |
| Perhydrosqualene | 18.000 g |
| Mixture of caprylic-capric triglycerides sold under the name "Miglyol 812" by "DYNAMIT NOBEL" | 4.000 g |
| Triethanolamine (99% by weight) | 2.500 g |
| Water | qs 100.000 g |

This cream is applied twice per day to a skin affected by inflammatory dermatosis for 30 days.

(j) The Following Cream of Oil-in-Water Type is Prepared:

| | |
|---|---|
| Lactic acid | 5.000 g |
| Compound of Example 1 | 0.020 g |
| S-carboxymethylcysteine | 3.000 g |

-continued

| | |
|---|---|
| Polyoxyethylene stearate (40 mol of ethylene oxide) sold under the name "Myrj 52" by "ATLAS" | 4.000 g |
| Polyoxyethylenated sorbitan monolaurate containing 20 mol of ethylene oxide sold under the name "Tween 20" by "ATLAS" | 1.800 g |
| Mixture of glycerol mono-and distearate sold under the name "Géléol" by "GATTEFOSSE" | 4.200 g |
| Propylene glycol | 10.000 g |
| Butylated hydroxyanisole | 0.010 g |
| Buytlated hydroxytoluene | 0.020 g |
| Cetylstearyl alcohol | 6.200 g |
| Preservatives | qs |
| Perhydrosqualene | 18.000 g |
| Mixture of caprylic-capric triglycerides sold under the name "Miglyo 812" "DYNAMIT NOBEL" | 4.000 g |
| Water | qs 100.000 g |

This cream is applied once per day; it combats aging whether photoinduced or chronologic.

(k) The Following Anhydrous Salve is Prepared:

| | |
|---|---|
| Compound of Example 3 | 5.000 g |
| Liquid paraffin | 50.00 g |
| Butylated hydroxytoluene | 0.050 g |
| Petroleum jelly | qs 100 g |

This salve is applied twice per day to a skin affected by squamose dermatosis for 30 days.

3) Intralesion Route:

(a) The Following Composition is Prepared:

| | |
|---|---|
| Compound of Example 1 | 0.002 g |
| Ethyl oleate | qs 10.0 g |

In the treatment of malignant melanoma, the composition is injected into an adult individual at a frequency of 1 to 7 times per week for 1 to 12 months.

(b) The Following Composition is Prepared:

| | |
|---|---|
| Compound of Example 2 | 0.050 g |
| Olive oil | qs 2.0 g |

In the treatment of basocellular carcinoma, the composition is injected into an adult individual at a frequency of 1 to 7 times per week for 1 to 12 months.

(c) The Following Composition is Prepared:

| | |
|---|---|
| Compound of Example 3 | 0.1 mg |
| Sesame oil | qs 2.0 g |

In the treatment of spinocellular carcinoma, the composition is injected into an adult individual at a frequency of 1 to 7 times per week for 1 to 12 months.

(d) The Following Composition is Prepared:

| | |
|---|---|
| Compound of Example 4 | 0.001 mg |
| Methyl benzoate | qs 10.0 g |

In the treatment of colon carcinoma, the composition is injected into an adult individual at a frequency of 1 to 7 times per week for 1 to 12 months.

(e) The Following Composition is Prepared:

| | |
|---|---|
| Compound of Example 2 | 0.001 g |
| Compound of Example 4 | 0.001 g |
| Ethyl oleate | qs 10.0 g |

In the treatment of malignant melanoma, the composition is injected into an adult individual at a frequency of 1 to 7 times per week for 1 to 12 months.

4) Intravenous Route:

(a) The Following Injectable Lipid Emulsion is Prepared:

| | |
|---|---|
| Compound of Example 1 | 0.001 mg |
| Soya bean oil | 10.000 g |
| Egg phospholipid | 1.200 g |
| Glycerin | 2.500 g |
| Water for injection | qs 100.000 g |

In the treatment of psoriasis, the composition is injected into an adult individual at a frequency of 1 to 7 times per week for 1 to 12 months.

(b) The Following Injectable Lipid Emulsion is Prepared:

| | |
|---|---|
| Compound of Example 3 | 0.010 g |
| Cottonseed oil | 10.000 g |
| Soya bean lecithin | 0.750 g |
| Sorbitol | 5.000 g |
| (DL)-α-Tocopherol | 0.100 g |
| Water for injection | qs 100.000 g |

In the treatment of iehthyosis, the composition is injected into an adult individual at a frequency of 1 to 7 times per week for 1 to 12 months.

(c) The Following Injectable is Prepared:

| | |
|---|---|
| Compound of Example 1 | 0.001 g |
| Soya bean oil | 15.000 g |
| Acetylated monoglycerides | 10.000 g |
| Pluronic F-108 | 1.000 g |
| Glycerol | 2.500 g |
| Water for injection | qs 100.000 g |

In the treatment of leukaemia, the composition is injected into an adult individual at a frequency of 1 to 7 times per week for 1 to 12 months.

(d) The Following Mixed Micell Composition is Prepared:

| | |
|---|---|
| Compound of Example 2 | 0.001 g |
| Lecithin | 16.930 g |
| Glycocholic acid | 8.850 g |
| Water for injection | qs 100.000 g |

In the treatment of malignant melanoma, the composition is injected into an adult individual at a frequency of 1 to 7 times per week for 1 to 12 months.

(e) The Following Cyclodextrin Composition is Prepared:
Compound of Example 1 0.05 mg
Compound of Example 2 0.05 mg
β-Cyclodextrin 0.100 g
Water for injection qs 10.000 g
In the treatment of graft rejection, the composition is injected into an adult individual at a frequency of 1 to 7 times per week for 1 to 12 months.

(f) The Following Cyclodextrin Composition is Prepared:
Compound of Example 3 0.010 g
2-Hydroxypropyl-β-cyclodextrin 0.100 g
Water for injection qs 10.000 g
In the treatment of kidney cancer, the composition is injected into an adult individual at a frequency of 1 to 7 times per week for 1 to 12 months.

EXAMPLE 6

Test for Evaluating the Biological Activity of the Compounds of the Invention—Activity on the Differentiation of HL60 Cells Calcitriol induces the differentiation of promyelocytic leukaemia cells (HL60) into monocytes/macrophages. This differentiation-inducing effect is a well characterized marker for cellular vitamin D. One of the most important antimicrobial products of macrophages is hydrogen peroxide, which may be analyzed experimentally by the reduction of NBT (Nitroblue Tetrazolium).

The method used is the following: the HL60 cells are inoculated into 6-well plates and then treated immediately with a test compound. After 4 days of culture, the cells are incubated with phorbol TPA ester and NBT for a short period and the differentiated cells, that is to say which are positive to NBT are counted.

The differentiation inducing effect on HL60 cells of the compounds according to the invention, and that of the reference compound calcitriol, are presented in Table I.

The results show that the compounds of Examples 1 and 2 have a differentiation-inducing activity on the HL60 cells which is weaker than that of calcitriol; these AC50 values are nevertheless significant and show the marked activity, in particular of the compound of Example 1, of the compounds according to the invention on the differentiation of HL60 cells.

TABLE I

| Compound Tested | AC50-HL60 (in nM) |
| --- | --- |
| Calcitriol | 10.7 |
| Compound of Example 1 | 312 |
| Compound of Example 2 | 2500 |

EXAMPLE 7

Tests for Evaluating the Biological Activity of the Compounds of the Invention—Measurement of the VDR Agonist Activity (AC50 hVDR)

The VDR agonist activity of the compounds of the invention may be tested on the HeLa cell line by co-transfection of the human VDR receptor expression vector and of the reporter plasmid p240Hase-CAT which contains the −1399 to +76 region of the rat 24-hydroxylase promoter, cloned upstream of the coding frame of the chloramphenicolacetyl transferase (CAT) gene. 18 hours after co-transfection, the compound to be tested is added to the medium. After 18 hours of treatment, the assay of the CAT activity of the cellular lysates is carried out by an ELISA test (Enzyme Linked Immuno Sorbent Assay, marketed by Roche Molecular Biochemicals). The agonist activity may be characterized in this co-transfection system by determining the dose required to reach 50% of the maximum activity of the compound tested (AC50).

The measurement of the VDR agonist activity of the compounds according to the invention and that of the reference compound, calcitriol, are presented in Table II.

As in Example 6, these results show that the compounds according to the present invention have activities which are weaker than that of calcitriol but nevertheless significant.

TABLE II

| Compound Tested | AC50-hVDR (in nM) |
| --- | --- |
| Calcitriol | 2.5 |
| Compound of Example 1 | 40 |
| Compound of Example 2 | 172 |
| Compound of Example 3 | 1211 |
| Compound of Example 4 | >3000 |

EXAMPLE 8

Tests for Evaluating the Biological Activity of the Compounds of the Invention—Activity on the Proliferation of Human Keratinocytes It is known that 1,25-dihydroxyvitamin D3, called calcitriol and corresponding to natural vitamin D, inhibits the proliferation of human keratinocytes in culture.

The method used is the following: normal human keratinocytes are inoculated at low density into a 24-well plate. After 4 hours, the compounds to be tested are added to the culture medium. After 5 days of culture, the proliferation of the kerátinocytes is determined by incorporating 5-bromo-2'-deoxyuridine (BrdU) into the DNA. The quantity of BrdU incorporated is then measured using the ELISA test (Enzyme Linked Immuno Sorbent Assay, marketed by Roche Molecular Biochemicals).

The inhibitory effect, on the proliferation of keratinocytes, of the compounds according to the invention and of calcitriol used as reference compound is summarized in Table III.

The IC50 value indicates the concentration of the compound tested for which the compound inhibits by 50% the proliferation of the keratinocytes.

These results show that the compounds of the invention have an inhibitory activity on the proliferation of keratinocytes which is lower than that of calcitriol; these compounds remain nevertheless of interest compared with the state of the art compounds.

TABLE III

| Activity Measured | IC50 - proliferation of the KHNs (in nM) |
| --- | --- |
| Calcitriol | 15.3 |
| Compound of Example 1 | 150 |
| Compound of Example 2 | 140 |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A biaromatic vitamin D analogue having the following general formula (I):

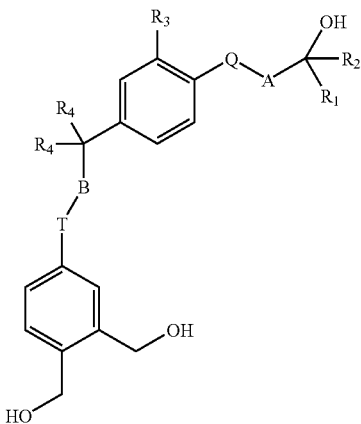

in which A-Q is an unsubstituted alkyne or alkene bond, a —$CH_2$—O— radical, a —$CH_2$—S— radical or a —$CH_2$—$CH_2$— radical; B-T is an unsubstituted alkyne or alkene bond, a —$CH_2$—S—, —$CH_2$—O—, —$CH_2$—$CH_2$— or —$CH_2$—$NR_6$— radical; $R_6$ is as defined below; $R_1$ and $R_2$, which may be identical or different, are each a hydrogen atom, a linear or branched alkyl radical having 1 to 5 carbon atoms, or the radical —$CF_2R_5$; $R_3$ is a linear or branched alkyl radical having 1 to 5 carbon atoms or the radical $CF_2R_5$; $R_5$ is as defined below; the radicals $R_4$, which may be identical, are each a hydrogen atom, a linear or branched alkyl radical having 1 to 6 carbon atoms, or the radical —$CF_2R_5$, with the proviso that the two radicals may also form a saturated ring having 4 to 7 carbon atoms, or a saturated heterocycle; $R_5$ is a fluorine atom, a hydrogen atom, or a radical —$CF_3$; $R_6$ is a hydrogen atom, a linear or branched alkyl radical having 1 to 6 carbon atoms, or the radical —$C(O)R_8$; and $R_8$ is a hydrogen atom, or a linear or branched alkyl radical having 1 to 6 carbon atoms; and the optical and geometric isomers and salts thereof.

2. The vitamin D analogue as defined by claim 1, wherein formula (I), A-Q is an alkyne or alkene bond.

3. The vitamin D analogue as defined by claim 1, wherein formula (I), A-Q is a —$CH_2$—O— radical.

4. The vitamin D analogue as defined by claim 1, wherein formula (I), A-Q is a —$CH_2$—S— radical.

5. The vitamin D analogue as defined by claim 1, wherein formula (I), A-Q is a —$CH_2$—$CH_2$— radical.

6. The vitamin D analogue as defined by claim 1, wherein formula (I), B-T is an alkyne or alkene bond.

7. The vitamin D analogue as defined by claim 1, wherein formula (I), B-T is a —$CH_2$—S— radical.

8. The vitamin D analogue as defined by claim 1, wherein formula (I), B-T is a —$CH_2$—O— radical.

9. The vitamin D analogue as defined by claim 1, wherein formula (I), B-T is a —$CH_2$—$CH_2$— radical.

10. The vitamin D analogue as defined by claim 1, wherein formula (I), B-T is a —$CH_2$—$NR_6$— radical.

11. The vitamin D analogue as defined by claim 1, wherein formula (I), at least one of $R_1$ and $R_2$ is the radical —$CF_2R_5$.

12. A biaromatic vitamin D analogue having the following general formula (I):

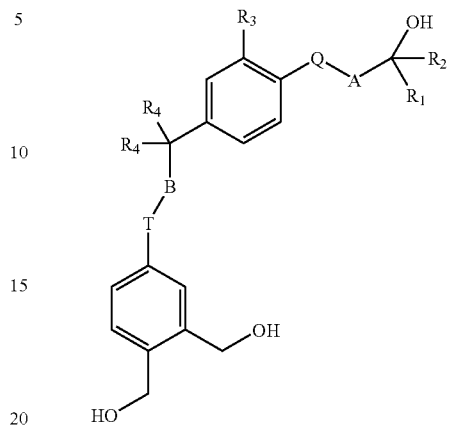

in which A-Q is an unsubstituted alkyne or alkene bond, a —$CH_2$—O— radical, a —$CH_2$—S— radical or a —$CH_2$—$CH_2$— radical; B-T is an unsubstituted alkyne or alkene bond, a —$CH_2$—S—, —$CH_2$—O—, —$CH_2$—$CH_2$— or —$CH_2$—$NR_6$— radical; $R_6$ is as defined below; $R_1$ and $R_2$, which may be identical or different, are each a hydrogen atom, a linear or branched alkyl radical having 1 to 5 carbon atoms, or the radical —$CF_2R_5$; $R_3$ is a linear or branched alkyl radical having 1 to 5 carbon atoms or the radical $CF_2R_5$; $R_5$ is as defined below; the radicals $R_4$, which may be identical, are each a hydrogen atom, a linear or branched alkyl radical having 1 to 6 carbon atoms, or the radical —$CF_2R_5$, with the proviso that the two radicals may also form a saturated ring having 4 to 7 carbon atoms, or a saturated heterocycle; $R_5$ is a fluorine atom, a hydrogen atom, or a radical —$CF_3$; $R_6$ is a hydrogen atom, a linear or branched alkyl radical having 1 to 6 carbon atoms, or the radical —$C(O)R_8$; and $R_8$ is a hydrogen atom, or a linear or branched alkyl radical having 1 to 6 carbon atoms; and the optical and geometric isomers and salts thereof, wherein formula (I), $R_3$ is the radical —$CF_2R_5$.

13. A biaromatic vitamin D analogue having the following general formula (I):

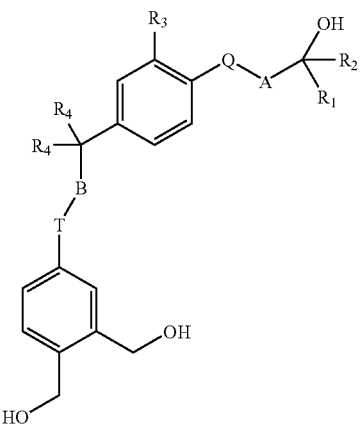

in which A-Q is an unsubstituted alkyne or alkene bond, a —$CH_2$—O— radical, a —$CH_2$—S— radical or a —$CH_2$—$CH_2$— radical; B-T is an unsubstituted alkyne or alkene bond, a —CH$_2$—S—, —CH$_2$—O—, —CH$_2$—CH$_2$— or —CH$_2$—NR$_6$— radical; R$_6$ is as defined below; R$_1$ and R$_2$, which may be identical or different, are each a hydrogen atom, a linear or branched alkyl radical having 1 to 5 carbon atoms, or the radical —CF$_2$R$_5$; R$_3$ is a linear or branched alkyl radical having 1 to 5 carbon atoms, or the radical CF$_2$R$_5$; R$_5$ is as defined below; the radicals R$_4$, which may be identical, are each a hydrogen atom, a linear or branched alkyl radical having 1 to 6 carbon atoms, or the radical —CF$_2$R$_5$, with the proviso that the two radicals may also form a saturated ring having 4 to 7 carbon atoms, or a saturated heterocycle; R$_5$ is a fluorine atom, a hydrogen atom, or a radical —CF$_3$; R$_6$ is a hydrogen atom, a linear or branched alkyl radical having 1 to 6 carbon atoms, or the radical —C(O)R$_8$; and R$_8$ is a hydrogen atom, or a linear or branched alkyl radical having 1 to 6 carbon atoms; and the optical and geometric isomers and salts thereof, wherein formula (I), at least one radical R$_4$ is the radical —CF$_2$R$_5$.

14. A biaromatic vitamin D analogue having the following general formula (I):

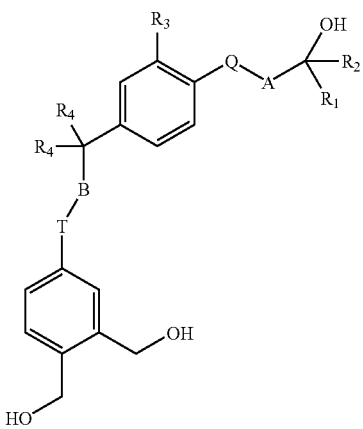

in which A-Q is an unsubstituted alkyne or alkene bond, a —CH$_2$—O— radical, a —CH$_2$—S— radical or a —CH$_2$—CH$_2$— radical; B-T is an unsubstituted alkyne or alkene bond, a —CH$_2$—S—, —CH$_2$—O—, —CH$_2$—CH$_2$— or —CH$_2$—NR$_6$— radical; R$_6$ is as defined below; R$_1$ and R$_2$, which may be identical or different, are each a hydrogen atom, a linear or branched alkyl radical having 1 to 5 carbon atoms, or the radical —CF$_2$R$_5$; R$_3$ is a linear or branched alkyl radical having 1 to 5 carbon atoms or the radical CF$_2$R$_5$; R$_5$ is as defined below; the radicals R$_4$, which may be identical, are each a hydrogen atom, a linear or branched alkyl radical having 1 to 6 carbon atoms, or the radical —CF$_2$R$_5$, with the proviso that the two radicals may also form a saturated ring having 4 to 7 carbon atoms, or a saturated heterocycle; R$_5$ is a fluorine atom, a hydrogen atom, or a radical —CF$_3$; R$_6$ is a hydrogen atom, a linear or branched alkyl radical having 1 to 6 carbon atoms, or the radical —C(O)R$_8$; and R$_8$ is a hydrogen atom, or a linear or branched alkyl radical having 1 to 6 carbon atoms; and the optical and geometric isomers and salts thereof, wherein formula (I), the radicals R$_4$, together with the carbon atom from which they depend, form a cyclobutyl, cyclopentyl, cyclohexyl or cycloheptyl ring member.

15. A biaromatic vitamin D analogue having the following general formula (I):

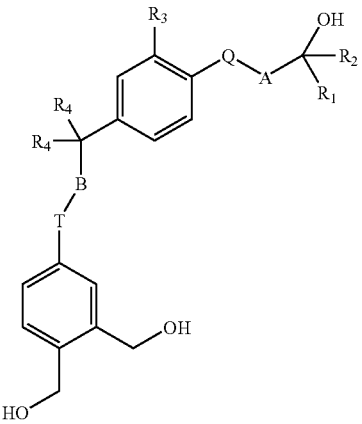

in which A-Q is an unsubstituted alkyne or alkene bond, a —CH$_2$—O— radical, a —CH$_2$—S— radical or a —CH$_2$—CH$_2$— radical; B-T is an unsubstituted alkyne or alkene bond, a —CH$_2$—S—, —CH$_2$—O—, —CH$_2$—CH$_2$— or —CH$_2$—NR$_6$— radical; R$_6$ is as defined below; R$_1$ and R$_2$, which may be identical or different, are each a hydrogen atom, a linear or branched alkyl radical having 1 to 5 carbon atoms, or the radical —CF$_2$R$_5$; R$_3$ is a linear or branched alkyl radical having 1 to 5 carbon atoms or the radical CF$_2$R$_5$; R$_5$ is as defined below; the radicals R$_4$, which may be identical, are each a hydrogen atom, a linear or branched alkyl radical having 1 to 6 carbon atoms, or the radical —CF$_2$R$_5$, with the proviso that the two radicals may also form a saturated ring having 4 to 7 carbon atoms, or a saturated heterocycle; R$_5$ is a fluorine atom, a hydrogen atom, or a radical —CF$_3$; R$_6$ is a hydrogen atom, a linear or branched alkyl radical having 1 to 6 carbon atoms, or the radical —C(O)R$_8$; and R$_8$ is a hydrogen atom, or a linear or branched alkyl radical having 1 to 6 carbon atoms; and the optical and geometric isomers and salts thereof, wherein formula (I), the radicals R$_4$, together with the carbon atom from which they depend, form a saturated heterocyclic selected from the group consisting of furan, pyran, pyrrolidine substituted on the nitrogen heteroatom with a radical R$_7$ and piperidine substituted on the nitrogen heteroatom with a radical R$_7$; in which R$_7$, which may be identical to or different from R$_8$, is also a hydrogen atom, or a linear or branched alkyl radical having 1 to 6 carbon atoms.

16. A salt of the vitamin D analogue as defined by claim 1, wherein formula (I) comprises a nitrogen atom.

17. A salt as defined by claim 16, of hydrochloric, sulphuric, acetic, fumaric, hemisuccinic, maleic or mandelic acid.

18. The vitamin D analogue as defined by claim 1, wherein formula (I) comprises at least one linear or branched alkyl radical selected from the group consisting of methyl, ethyl, n-propyl, i-propyl, n-butyl, i-butyl, t-butyl, n-pentyl, 1-methylbutyl, 3-methylbutyl 2,2-dimethypropyl, n-hexyl, 4-methylpentyl, 3,3-dimethylbutyl and 2,2-dimethylbutyl radicals.

19. The vitamin D analogue as defined by claim 1, selected from the group consisting of:
  1. 1-{4-[3-(3,4-Bis-hydroxymethyl-phenyl)-propyl]-2-ethyl-phenoxy]-3,3-dimethyl-butan-2-ol;

2. 1-{4-[3-(3,4-Bis-hydroxymethyl-phenyl)-propyl]-2-methyl-phenoxy}-3,3-dimethyl-butan-2-ol;
3. (4-{3-[3-ethyl-4-(2-ethyl-2-hydroxy-butoxy)-phenyl]-propyl}-2-hydroxymethyl-phenyl)-methanol;
4. (4-{3-[4-(2-ethyl-2-hydroxy-butoxy)-3-methyl-phenyl]-propyl}-2-hydroxymethyl-phenyl)-methanol;
5. (2-hydroxymethyl-4-{3-[4-(2-hydroxy-3-methyl-phenyl-butoxy)-3-methyl-phenyl]-propyl}-phenyl)-methanol;
6. (4-{3-[3-ethyl-4-(2-hydroxy-3-methyl-butoxy)-phenyl]-propyl}-2-hydroxymethyl-phenyl)-methanol;
7. (2-hydroxymethyl-4-{3-[4-(2-hydroxy-3-methyl-butylsulphanyl)-3-methyl-phenyl]-propyl-phenyl)-methanol;
8. (4-{3-[3-ethyl-4-(2-hydroxy-3-methyl-butylsulphanyl)-phenyl]-propyl}-2-hydroxymethyl-phenyl)-methanol;
9. (2-hydroxymethyl-4-{3-[4-(3-hydroxy-4-methyl-pentyl)-3-methyl-phenyl]-propyl}-phenyl)-methanol;
10. (4-{3-[3-ethyl-4-(3-hydroxy-4-methyl-pentyl)-phenyl]-propyl}-2-hydroxymethyl-phenyl)-methanol;
11. (E)-1-{4-[3-(3,4-bis-hydroxymethyl-phenyl)-propyl]-2-methyl-phenyl}-4-methyl-pent-1-en-3-ol;
12. (E)-1-{4-[3-(3,4-bis-hydroxymethyl-phenyl)-propyl]-2-ethyl-phenyl}-4-methyl-pent-1-en-3-ol;
13. (4-{3-[4-(2-hydroxy-3,3-dimethyl-butylsulphanyl)-3-methyl-phenyl]-propyl}-2-hydroxymethyl-phenyl)-methanol;
14. (4-{3-[3-ethyl-4-(2-hydroxy-3,3-dimethyl-butylsulphanyl)-phenyl]-propyl)-2-hydroxymethyl-phenyl)-methanol;
15. (4-{3-[4-(3-hydroxy-4,4-dimethyl-pentyl)-3-methyl-phenyl]-propyl}-2-hydroxymethyl-phenyl)-methanol;
16. (4-{3-[3-ethyl-4-(3-hydroxy-4,4-dimethyl-pentyl)-phenyl]-propyl}-2-hydroxymethyl-phenyl)-methanol;
17. (E)-1-{4-[3-(3,4-bis-hydroxymethyl-phenyl)-propyl]-2-methyl-phenyl}-4,4-dimethyl-pent-1-en-3-ol;
18. (E)-1-{4-[3-(3,4-bis-hydroxymethyl-phenyl)-propyl]-2-ethyl-phenyl}-4,4-dimethyl-pent-1-en-3-ol;
19. (2-hydroxymethyl-4-{3-[3-methyl-4-)(3,3,3-trifluoro-2-hydroxy-propoxy)-phenyl]-propyl}-phenyl)-methanol;
20. (4-{3-[3-ethyl-4-(3,3,3-trifluoro-2-hydroxy-propoxy)-phenyl]-propyl}-2-hydroxymethyl-phenyl)-methanol;
21. (2-hydroxymethyl-4-{3-[3-methyl-4-(3,3,3-trifluoro-2-hydroxy-propylsulphanyl)-phenyl]-propyl}-phenyl)-methanol;
22. (4-{3-[3-ethyl-4-(3,3,3-trifluoro-2-hydroxy-propylsulphanyl)-phenyl]-propyl}-2-hydroxymethyl-phenyl)-methanol;
23. (2-hydroxymethyl-4-{3-[3-methyl-4-(4,4,4-trifluoro-3-hydroxy-butyl)-phenyl]-propyl}-phenyl)-methanol;
24. (4-{3-[3-ethyl-4-(4,4,4-trifluoro-3-hydroxy-butyl)-phenyl]-propyl}-2-hydroxymethyl-phenyl)-methanol;
25. (2-hydroxymethyl-4-{3-[3-methyl-4-((E)-4,4,4-trifluoro-3-hydroxy-but-1-enyl)-phenyl]-propyl}phenyl)-methanol;
26. (4-{3-[3-ethyl-4-((E)-4,4,4-trifluoro-3-hydroxy-but-1-enyl)-phenyl]-propyl}-2-hydroxymethyl-phenyl)-methanol;
27. (2-hydroxymethyl-4-{3-[3-methyl-4-(4,4,4-trifluoro-2-hydroxy-3-trifluoromethyl-butoxy)-phenyl]-propyl}-phenyl)-methanol;
28. (4-{3-[3-ethyl-4-(4,4,4-trifluoro-2-hydroxy-3-trifluoromethyl-butoxy)-phenyl]-propyl)-2-hydroxymethyl-phenyl)-methanol;
29. (2-hydroxymethyl-4-{3-[3-methyl-4-(4,4,4-trifluoro-2-hydroxy-3-trifluoromethyl-butylsulphanyl)-phenyl]-propyl}-phenyl)-methanol;
30. (4-{3-[3-ethyl-4-(4,4,4-trifluoro-2-hydroxy-3-trifluoromethyl-butylsulphanyl)-phenyl]-propyl}-2-hydroxymethyl-phenyl)-methanol;
31. (2-hydroxymethyl-4-{3-[methyl-(5,5,5-trifluoro-3-hydroxy-4-trifluoromethyl-pentyl)-phenyl]-propyl}-phenyl)-methanol;
32. (4-{3-[ethyl-(5,5,5-trifluoro-3-hydroxy-4-trifluoromethyl-pentyl)-phenyl]-propyl}-2-hydroxymethyl-phenyl)-methanol;
33. (E)-{4-[3-(3,4-bis-hydroxymethyl-phenyl)-propyl]-2-methyl-phenyl}-5,5,5-trifluoro-4-trifluoromethyl-pent-1-en-3-ol;
34. (E)-{4-[3-(3,4-bis-hydroxymethyl-phenyl)-propyl]-2-ethyl-phenyl}-5,5,5-trifluoro-4-trifluoromethyl-pent-1-en-3-ol;
35. (2-hydroxymethyl-4-{3-[4-(2-hydroxy-3-methyl-butoxy)-3-methyl-phenyl]-3-methyl-butyl}-phenyl)-methanol;
36. (4-{3-[3-ethyl-4-(2-hydroxy-3-methyl-butoxy)phenyl]-3-methyl-butyl}-2-hydroxymethyl-phenyl)-methanol;
37. (2-hydroxymethyl-4-{3-[4-(2-hydroxy-3-methyl-butylsulphanyl)-3-methyl-phenyl]-3-methyl-butyl}-phenyl)-methanol;
38. (4-(3-[3-ethyl-4-(2-hydroxy-3-methyl-butylsulphanyl)-phenyl]-3-methyl-butyl}-2-hydroxymethyl-phenyl)-methanol;
39. (2-hydroxymethyl-4-{3-[4-(3-hydroxy-4-methyl-pentyl)-3-methyl-phenyl]-3-methyl-butyl}-phenyl)-methanol;
40. (4-{3-[3-ethyl-4-(3-hydroxy-4-methyl-pentyl)-phenyl]-3-methyl-butyl}-2-hydroxymethyl-phenyl)-methanol;
41. (E)-1-{4-[3-(3,4-bis-hydroxymethyl-phenyl)-1,1-dimethyl-propyl]-2-methyl-phenyl}-4-methyl-pent-1-en-3-ol;
42. (E)-1-{4-[3-(3,4-bis-hydroxymethyl-phenyl)-1,1-dimethyl-propyl]-2-ethyl-phenyl}-4-methyl-pent-1-en-3-ol;
43. (4-{3-[4-(2-hydroxy-3,3-dimethyl-butoxy)-3-methyl-phenyl]-3-methyl-butyl}-2-hydroxymethyl-phenyl)-methanol;
44. (4-{3-[3-ethyl-4-(2-hydroxy-3,3-dimethyl-butoxy)-phenyl]-3-methyl-butyl}-2-hydroxymethyl-phenyl)-methanol;
45. (4-{3-[4-(2-hydroxy-3,3-dimethyl-butylsulphanyl)-3-methyl-phenyl]-3-methyl-butyl)-2-hydroxymethyl-phenyl)-methanol;
46. (4-{3-[3-ethyl-4-(2-hydroxy-3,3-dimethyl-butylsulphanyl)-phenyl]-3-methyl-butyl}-2-hydroxymethyl-phenyl)-methanol;
47. (4-{3-[4-(3-hydroxy-4,4-dimethyl-pentyl)-3-methyl-phenyl]-3-methyl-butyl}-2-hydroxymethyl-phenyl)-methanol;
48. (4-{3-[3-ethyl-4-(3-hydroxy-4,4-dimethyl-pentyl)-phenyl]-3-methyl-butyl}-2-hydroxymethyl-phenyl)-methanol;
49. (E)-1-{4-[3-(3,4-bis-hydroxymethyl-phenyl)-1,1-dimethyl-propyl]-2-methyl-phenyl}-4,4-dimethyl-pent-1-en-3-ol;
50. (E)-1-{4-[3-(3,4-bis-hydroxymethyl-phenyl)-1,1-dimethyl-propyl]-2-ethyl-phenyl}-4,4-dimethyl-pent-1-en-3-ol;

51. (4-{3-ethyl-3-[4-(2-hydroxy-3-methyl-butoxy)-3-methyl-phenyl]-pentyl-2-hydroxymethyl-phenyl)-methanol;
52. (4-{3-ethyl-3-[3-ethyl-4-(2-hydroxy-3-methyl-butoxy)-phenyl]-pentyl}-2-hydroxymethyl-phenyl)-methanol;
53. (4-{3-ethyl-3-[4-(2-hydroxy-3-methyl-butylsulphanyl)-3-methyl-phenyl]-pentyl}-2-hydroxymethyl-phenyl)-methanol;
54. (4-{3-ethyl-3-[3-ethyl-4-(2-hydroxy-3-methyl-butylsulphanyl)-phenyl]-pentyl}-2-hydroxymethyl-phenyl)-methanol;
55. (4-{3-ethyl-3-[4-(3-hydroxy-4-methyl-pentyl)-3-methyl-phenyl]-pentyl}-2-hydroxymethyl-phenyl)-methanol;
56. (4-{3-ethyl-3-[3-ethyl-4-(3-hydroxy-4-methyl-pentyl)-phenyl]-pentyl}-2-hydroxymethyl-phenyl)-methanol;
57. (E)-1-{4-[3-(3,4-bis-hydroxymethyl-phenyl)-1,1-diethyl-propyl]-2-methyl-phenyl}-4-methyl-pent-1-en-3-ol;
58. (E)-1-{4-[3-(314-bis-hydroxymethyl-phenyl)-1,1-diethyl-propyl]-2-ethyl-phenyl}-4-methyl-pent-1-en-3-ol;
59. (4-{3-ethyl-3-[4-(2-hydroxy-3,3-dimethyl-butoxy)-3-methyl-phenyl]-pentyl}-2-hydroxymethyl-phenyl)-methanol;
60. (4-{3-ethyl-3-[3-ethyl-4-(2-hydroxy-3,3-dimethyl-butoxy)-phenyl]-pentyl}-2-hydroxymethyl-phenyl)-methanol;
61. (4-{3-ethyl-3-[4-(2-hydroxy-3,3-dimethyl-butylsulphanyl)-3-methyl-phenyl]-pentyl}-2-hydroxymethyl-phenyl)-methanol;
62. (4-{3-ethyl-3-[3-ethyl-4-(2-hydroxy-3,3-dimethyl-butylsulphanyl)-phenyl]-pentyl}-2-hydroxymethyl-phenyl)-methanol;
63. 4-{3-ethyl-3-[4-(3-hydroxy-4,4-dimethyl-pentyl)-3-methyl-phenyl]-pentyl}-2-hydroxymethyl-phenyl)-methanol;
64. (4-{3-ethyl-3-[3-ethyl-4-(3-hydroxy-4,4-dimethyl-pentyl)-phenyl]-pentyl}-2-hydroxymethyl-phenyl)-methanol;
65. (E)-1-{4-[3-(3,4-bis-hydroxymethyl-phenyl)-1,1-diethyl-propyl]-2-methyl-phenyl}-4,4-dimethyl-pent-1-en-3-ol;
66. (E)-1-{4-[3-(3,4-bis-hydroxymethyl-phenyl)-1,1-diethyl-propyl]-2-ethyl-phenyl}-4,4-dimethyl-pent-1-en-3-ol;
67. [2-hydroxymethyl-4-(2-{1-[4-(2-hydroxy-3-methyl-butoxy)-3-methyl-phenyl]-cyclopentyl}-ethyl)-phenyl]-methanol;
68. [4-(2-{1-[3-ethyl-4-(2-hydroxy-3-methyl-butoxy)-phenyl]-cyclopentyl}-ethyl)-2-hydroxymethyl-phenyl]-methanol;
69. [2-hydroxymethyl-4-(2-{1-[4-(2-hydroxy-3-methyl-butylsulphanyl)-3-methyl-phenyl]-cyclopentyl}-ethyl)-phenyl]-methanol;
70. [4-(2-{1-[3-ethyl-4-(2-hydroxy-3-methyl-butylsulphanyl)-phenyl]-cyclopentyl}-ethyl)-2-hydroxymethyl-phenyl]-methanol;
71. [2-hydroxymethyl-4-(2-{1-[4-(3-hydroxy-4-methyl-pentyl)-3-methyl-phenyl]-cyclopentyl}-ethyl)-phenyl]-methanol;
72. [4-(2-{1-[3-ethyl-4-(3-hydroxy-4-methyl-pentyl)-phenyl]-cyclopentyl}-ethyl)-2-hydroxymethyl-phenyl]-methanol;
73. (E)-1-(4-{1-[2-(3,4-bis-hydroxymethyl-phenyl)-ethyl]-cyclopentyl}-2-methyl-phenyl)-4-methyl-pent-1-en-3-ol;
74. (E)-1-(4-{1-[2-(3,4-bis-hydroxymethyl-phenyl)-ethyl]-cyclopentyl}-2-ethyl-phenyl)-4-methyl-pent-1-en-3-ol;
75. [4-(2-{1-[4-(2-hydroxy-3,3-dimethyl-butoxy)-3-methyl-phenyl]-cyclopentyl}-ethyl)-2-hydroxymethyl-phenyl]-methanol;
76. [4-(2-{1-[3-ethyl-4-(2-hydroxy-3,3-dimethyl-butoxy)-phenyl]-cyclopentyl}-ethyl)-2-hydroxymethyl-phenyl]-methanol;
77. [4-(2-{1-[4-(2-hydroxy-3,3-dimethyl-butylsulphanyl-3-methyl-phenyl]-cyclopentyl}-ethyl)-2-hydroxymethyl-phenyl]-methanol;
78. [4-(2-{1-[3-ethyl-4-(2-hydroxy-3,3-dimethyl-butylsulphanyl)-phenyl]-cyclopentyl}-ethyl)-2-hydroxymethyl-phenyl]-methanol;
79. [4-(2-{1-[4-(3-hydroxy-4,4-dimethyl-pentyl)-3-methyl-phenyl]-cyclopentyl}-ethyl)-2-hydroxymethyl-phenyl]-methanol;
80. [4-(2-{1-[3-ethyl-4-(3-hydroxy-4,4-dimethyl-pentyl)-phenyl]-cyclopentyl}-ethyl)-2-hydroxymethyl-phenyl]-methanol;
81. (E)-1-(4-{1-[2-(3,4-bis-hydroxymethyl-phenyl)-ethyl]-cyclopentyl}-2-methyl-phenyl)-4,4-dimethyl-pent-1-en-3-ol;
82. (E)-1-(4-{1-[2-(3,4-bis-hydroxymethyl-phenyl)-ethyl]-cyclopentyl}-2-ethyl-phenyl)-4,4-dimethyl-pent-1-en-3-ol;
83. [2-hydroxymethyl-4-(2-{1-[4-(2-hydroxy-3-methyl-butoxy)-3-methyl-phenyl]-cyclohexyl}-ethyl)-phenyl]-methanol;
84. [4-(2-{1-[3-ethyl-4-(2-hydroxy-3-methyl-butoxy)-phenyl]-cyclohexyl}-ethyl)-2-hydroxymethyl-phenyl]-methanol;
85. [2-hydroxymethyl-4-(2-{1-[4-(2-hydroxy-3-methy-butylsulphanyl)-3-methyl-phenyl]-cyclohexyl}-ethyl)-phenyl]-methanol;
86. [4-(2-{1-[3-ethyl-4-(2-hydroxy-3-methyl-butylsulphanyl)-phenyl]-cyclohexyl}-ethyl)-2-hydroxymethyl-phenyl]-methanol;
87. [2-hydroxymethyl-4-(2-{1-[4-(3-hydroxy-4-methyl-pentyl)-3-methyl-phenyl]-cyclohexyl}-ethyl)-phenyl]-methanol;
88. [4-(2-{1-[3-ethyl-4-(3-hydroxy-4-methyl-pentyl)-phenyl]-cyclohexyl}-ethyl)-2-hydroxymethyl-phenyl]-methanol;
89. (E)-1-(4-{1-[2-(3,4-bis-hydroxymethyl-phenyl)-ethyl]-cyclohexyl}-2-methyl-phenyl)-4-methyl-pent-1-en-3-ol;
90. (E)-1-(4-{1-[2-(3,4-bis-hydroxymethyl-phenyl)-ethyl]-cyclohexyl}-2-ethyl-phenyl)-4-methyl-pent-1-en-3-ol;
91. [4-(2-{1-[4-(2-hydroxy-3,3-dimethyl-butoxy)-3-methyl-phenyl]-cyclohexyl}-ethyl)-2-hydroxymethyl-phenyl]-methanol;
92. [4-(2-{1-[3-ethyl-4-(2-hydroxy-3,3-dimethyl-butoxy)-phenyl]-cyclohexyl}-ethyl)-2-hydroxymethyl-phenyl]-methanol;
93. [4-(2-{1-[4-(2-hydroxy-3,3-dimethyl-butylsulphanyl)-3-methyl-phenyl]-cyclohexyl}-ethyl)-2-hydroxymethyl-phenyl]-methanol;
94. [4-(2-{1-[3-ethyl-4-(2-hydroxy-3,3-dimethyl-butylsulphanyl)-phenyl]-cyclohexyl}-ethyl)-2-hydroxymethyl-phenyl]-methanol;

95. [4-(2-{1-[4-(3-hydroxy-4,4-dimethyl-pentyl)-3-methyl-phenyl]-cyclohexyl}-ethyl)-2-hydroxymethyl-phenyl]-methanol;
96. [4-(2-{1-[3-ethyl-4-(3-hydroxy-4,4-dimethyl-pentyl)-phenyl]-cyclohexyl}-ethyl)-2-hydroxymethyl-phenyl]-methanol;
97. (E)-1-(4-{1-[2-(3,4-bis-hydroxymethyl-phenyl)-ethyl]-cyclohexyl}-2-methyl-phenyl)-4,4-dimethyl-pent-1-en-3-ol;
98. (E)-1-(4-{1-[2-(3,4-bis-hydroxymethyl-phenyl)-ethyl]-cyclohexyl}-2-ethyl-phenyl)-4,4-dimethyl-pent-1-en-3-ol;
99. (4-{2-ethyl-2-[4-(2-hydroxy-3-methyl-butoxy)-3-methyl-phenyl]-butoxy}-2-hydroxymethyl-phenyl)-methanol;
100. (4-{2-ethyl-2-[3-ethyl-4-(2-hydroxy-3-methyl-butoxy)-phenyl]-butoxy}-2-hydroxymethyl-phenyl)-methanol;
101. (4-{2-ethyl-2-[4-(2-hydroxy-3-methyl-butylsulphanyl)-3-methyl-phenyl]-butoxy}-2-hydroxymethyl-phenyl)-methanol;
102. (4-{2-ethyl-2-[3-ethyl-4-(2-hydroxy-3-methyl-butylsulphanyl)-phenyl]-butoxy}-2-hydroxymethyl-phenyl)-methanol;
103. (4-{2-ethyl-2-[4-(3-hydroxy-4-methyl-pentyl)-3-methyl-phenyl]-butoxy}-2-hydroxymethyl-phenyl)-methanol;
104. (4-{2-ethyl-2-[3-ethyl-4-(3-hydroxy-4-methyl-pentyl)-phenyl]-butoxy}-2-hydroxymethyl-pentyl)-methanol;
105. (E)-1-{4-[1-(3,4-bis-hydroxymethyl-phenoxymethyl)-1-ethyl-propyl]-2-methyl-phenyl}-4-methyl-pen-1-en-3-ol;
106. (E)-1-{4-[1-(3,4-bis-hydroxymethyl-phenoxymethyl)-1-ethyl-propyl]-2-ethyl-phenyl}-4-methyl-pen-1-en-3-ol;
107. (4-{2-ethyl-2-[4-(2-hydroxy-3,3-dimethyl-butoxy)-3-methyl-phenyl]-butoxy}-2-hydroxymethyl-phenyl)-methanol;
108. (4-{2-ethyl-2-[3-ethyl-4-(2-hydroxy-3,3-dimethyl-butoxy)-phenyl]-butoxy}-2-hydroxymethyl-phenyl)-methanol;
109. (4-{2-ethyl-2-[4-(2-hydroxy-3,3-dimethyl-butylsulphanyl)-3-methyl-phenyl]-butoxy}-2-hydroxymethyl-phenyl)-methanol;
110. (4-{2-ethyl-2-[3-ethyl-4-(2-hydroxy-3,3-dimethyl-butylsulphanyl)-phenyl]-butoxy}-2-hydroxymethyl-phenyl)-methanol;
111. (4-{2-ethyl-2-[4-(3-hydroxy-4,4-dimethyl-pentyl)-3-methyl-phenyl]-butoxy}-2-hydroxymethyl-phenyl)-methanol;
112. (4-{2-ethyl-2-[3-ethyl-4-(3-hydroxy-4,4-dimethyl-pentyl)-phenyl]-butoxy}-2-hydroxymethyl-phenyl)-methanol;
113. (E)-1-{4-[1-(3,4-bis-hydroxymethyl-phenoxymethyl)-1-ethyl-propyl]-2-methyl-phenyl}-4,4-dimethyl-pent-1-en-3-ol;
114. (E)-1-{4-[1-(3,4-bis-hydroxymethyl-phenoxymethyl)-1-ethyl-propyl]-2-ethyl-phenyl}-4,4-dimethyl-pent-1-en-3-ol;
115. (4-{(E)-3-ethyl-3-[4-2-hydroxy-3-methyl-butoxy)-3-methyl-phenyl]-pent-1-enyl}-2-hydroxymethyl-phenyl)-methanol;
116. (4-{(E)-3-ethyl-3-[3-ethyl-4-(2-hydroxy-3-methyl-butoxy)-phenyl]-pent-1-enyl}-2-hydroxymethyl-phenyl)-methanol;
117. (4-{(E)-3-ethyl-3-[4-(2-hydroxy-3-methyl-butylsulphanyl)-3-methyl-phenyl]-pent-1-enyl}-2-hydroxymethyl-phenyl)-methanol;
118. (4-{(E)-3-ethyl-3-[3-ethyl-4-(2-hydroxy-3-methyl-butylsulphanyl)-phenyl]-pent-1-enyl}-2-hydroxymethyl-phenyl)-methanol;
119. (4-{(E)-3-ethyl-3-[4-(3-hydroxy-4-methyl-pentyl)-3-methyl-phenyl]-pent-1-enyl}-2-hydroxymethyl-phenyl)-methanol;
120. (4-{(E)-3-ethyl-3-[3-ethyl-4-(3-hydroxy-4-methyl-pentyl)-phenyl]-pent-1-enyl}-2-hydroxymethyl-phenyl)-methanol;
121. (E)-1-{4-[(E)-3-(3,4-bis-hydroxymethyl-phenyl)-1,1-diethyl-allyl]-2-methyl-phenyl}-4-methyl-pent-1-en-3-ol;
122. (E)-1-{4-[(E)-3-(3,4-bis-hydroxymethyl-phenyl)-1,1-diethyl-allyl]-2-ethyl-phenyl}-4-methyl-pent-1-en-3-ol;
123. (4{(E)-3-ethyl-3-3[4-(2-hydroxy-3,3-dimethyl-butoxy)-3-methyl-phenyl]pent-1-enyl}-2-hydroxymethyl-phenyl)-methanol;
124. (4-{(E)-3-ethyl-3-[3-ethyl-4-(2-hydroxy-3,3-dimethyl-butoxy)-phenyl]-pent-1-enyl}-2-hydroxymethyl-phenyl)-methanol;
125. (4-{(E)-3-ethyl-3-[4-(2-hydroxy-3,3-dimethyl-butylsulphanyl)3-methyl-phenyl]-pent-1-enyl}-2-hydroxymethyl-phenyl)-methanol;
126. (4-{(E)-3-ethyl-3-[3-ethyl-4-(2-hydroxy-3,3-dimethyl-butylsulphanyl)-phenyl]-pent-1-enyl}-2-hydroxymethyl-phenyl)-methanol;
127. (4-{(E)-3-ethyl-3-4-(3-hydroxy-4,4-dimethyl-pentyl)-3-methyl-phenyl]-pent-1-enyl}-2-hydroxymethyl-phenyl)-methanol;
128. (4-{(E)-3-ethyl-3-[3-ethyl-4-(3-hydroxy-4,4-dimethyl-pentyl)-phenyl]-pent-1-enyl}-2-hydroxymethyl-phenyl)-methanol;
129. (E)-1-{4-[(E)-3-(3,4-bis-hydroxymethyl-phenyl)-1,1-diethyl-allyl]-2-methyl-phenyl}-4,4-dimethyl-pent-1-en-3-ol;
130. (E)-1-{4-[(E)-3-(3,4-bis-hydroxymethyl-phenyl)-1,1-diethyl-allyl]-2-ethyl-phenyl}-4,4-dimethyl-pent-1-en-3-ol;
131. (4-{3-[3-ethyl-4-(3,3,3-trifluoro-2-hydroxy-propoxy)-phenyl]-3-methyl-butyl}-2-hydroxymethyl-phenyl)-methanol;
132. (4-{3-[3-ethyl-4-(3,3,3-trifluoro-2-hydroxy-propylsulphanyl)-phenyl]-3-methyl-butyl}-2-hydroxymethyl-phenyl)-methanol;
133. (4-{3-[3-ethyl-4-(4,4,4-trifluoro-3-hydroxy-butyl)-phenyl]-3-methyl-butyl}-2-hydroxymethyl-phenyl)-methanol;
134. (4-{3-[3-ethyl-4-((E)-4,4,4-trifluoro-3-hydroxy-but-1-enyl)-phenyl]-3-methyl-butyl}-2-hydroxymethyl-phenyl)-methanol;
135. (4-{3-[3-ethyl-4-(4,4,4-trifluoro-2-hydroxy-3-trifluoromethyl-butoxy)-phenyl]-3-methyl-butyl}-2-hydroxymethyl-phenyl)-methanol;
136. (4-{3-[3-ethyl-4-(4,4,4-trifluoro-2-hydroxy-3-trifluromethyl-butysulphanyl)-phenyl]-3-methyl-butyl}-2-hydroxymethyl-phenyl)-methanol;
137. (4-{[ethyl-(5,5,5-trifluoro-3-hydroxy-4-trifluoromethyl-pentyl)-phenyl]-methyl-butyl}-2-hydroxymethyl-phenyl)-methanol;
138. (E)-{4-[3-(3,4,bis-hydroxymethyl-phenyl)-1,1-dimethyl-propyl]-2-ethyl-phenyl}-5,5,5-trifluoro-4-trifluoromethyl-pent-1-en-ol;

139. (4-{3-ethyl-3-[3-ethyl-4-(3,3,3-trifluoro-2-hydroxy-propoxy)-phenyl]-pentyl}-2-hydroxymethyl-phenyl)-methanol;
140. (4-{3-ethyl-3-[3-ethyl-4-(3,3,3-trifluoro-2-hydroxy-propylsulphanyl)-phenyl]-pentyl}-2-hydroxymethyl-phenyl)-methanol;
141. (4-{3-ethyl-3-[3-ethyl-4-(4,4,4-trifluoro-3-hydroxy-butyl)-phenyl]-pentyl}-2-hydroxymethyl-phenyl)-methanol;
142. (4-{3-ethyl-3-[3-ethyl-4((E)-4,4,4-trifluoro-3-hydroxy-but-1-enyl)-phenyl]-pentyl}-2-hydroxymethyl-phenyl)-methanol;
143. (4-{3-ethyl-3-[3-ethyl-4-(4,4,4-trifluoro-2-hydroxy-3-trifluoromethyl-butoxy)-phenyl]-pentyl}-2-hydroxymethyl-phenyl)-methanol;
144. (4-{3-ethyl-3-[3-ethyl-4-(4,4,4-trifluoro-2-hydroxy-3-trifluoromethyl-butylsulphanyl)-phenyl]-pentyl}-2-hydroxymethyl-phenyl)-methanol;
145. (4-{ethyl-[ethyl-(5,5,5-trifluoro-3-hydroxy-4-trifluoromethyl-pentyl)-phenyl]-pentyl}-2-hydroxymethyl-pheflyl)-methanol;
146. (E)-{4-[3-(3,4-bis-hydroxymethyl-phenyl)-1,1-diethyl-propyl]-2-ethyl-phenyl}-5,5,5-trifluoro-4-trifluoromethyl-pent-1-en-3-ol
147. [4-(2-{1-[3-ethyl-4-(3,3,3-trifluoro-2-hydroxy-propoxy)-phenyl]-cyclohexyl}-ethyl)-2-hydroxymethyl-phenyl]-methanol;
148. [4-(2-{1-[3-ethyl-4-(3,3,3-trifluoro-2-hydroxy-propylsulphanyl)-phenyl]-cyclohexyl}-ethyl)-2-hydroxymethyl-phenyl]-methanol;
149. [4-(2-{1-[3-ethyl-4-(4,4,4-trifluoro-3-hydroxy-butyl)-phenyl]-cyclohexyl}-ethyl)-2-hydroxymethyl-phenyl]-methanol;
150. [4-(2-{1-[3-ethyl-4-((E)-4,4,4-trifluoro-3-hydroxy-but-1-enyl)-phenyl]-cyclohexyl}-ethyl)-2-hydroxymethyl-phenyl]-methanol;
151. [4-(2-{1-[3-ethyl-4-(4,4,4-trifluoro-2-hydroxy-3-trifluoromethyl-butoxy)-phenyl]-cyclohexyl}-ethyl)-2-hydroxymethyl-phenyl]-methanol;
152. [4-(2-{1-[3-ethyl-4-(4,4,4-trifluoro-2-hydroxy-3-trifluoromethyl-butysulphanyl)-phenyl]-cyclohexyl}-ethyl)-2-hydroxymethyl-phenyl]-methanol;
153. [4-(2-{1-[ethyl-(5,5,5-trifluoro-3-hydroxy-4-trifluoromethyl-pentyl)-phenyl]-cyclohexyl}-ethyl)-2-hydroxymethyl-phenyl]-methanol;
154. (E)-[4-(1-[2-(3,4-bis-hydroxymethyl-phenyl)-ethyl]-cyclohexyl}-2-ethyl-phenyl)-5,5,5-trifluoro-4-trifluoromethyl-pent-1-en-3-ol;
155. (4-{2-ethyl-2-[3-ethyl-4-(3,3,3-trifluoro-2-hydroxy-propoxy)-phenyl]-butoxy}-2-hydroxymethyl-phenyl-methanol;
156. (4-{2-ethyl-2-[3-ethyl-4-(3,3,3-trifluoro-2-hydroxy-propylsulphanyl)-phenyl]-butoxy}-2-hydroxymethyl-phenyl)-methanol;
157. (4-{2-ethyl-2-[3-ethyl-4-(4,4,4-trifluoro-3-hydroxy-butyl)-phenyl]-butoxy}-2-hydroxymethyl-phenyl)-methanol;
158. (4-{2-ethyl-2-[3-ethyl-4-((E)-4,4,4-trifluoro-3-hydroxy-but-1-enyl)-phenyl]-butoxy}-2-hydroxymethyl-phenyl)-methanol;
159. (4-{2-ethyl-2-[3-ethyl-4-(4,4,4-trifluoro-2-hydroxy-3-trifluoromethyl-butoxy)-phenyl]-butoxy}-2-hydroxymethyl-phenyl)-methanol;
160. (4-{2-ethyl-2-[3-ethyl-4-(4,4,4-trifluoro-2-hydroxy-3-trifluoromethy-butylsulphanyl)-phenyl]-butoxy}-2-hydroxymethyl-phenyl)-methanol;
161. (4-{ethyl-[ethyl-(5,5,5-trifluoro-3-hydroxy-4-trifluoromethyl-pentyl)-phenyl]-butoxy}-2-hydroxymethyl-phenyl)-methanol;
162. (E)-{4-[1-(3,4-bis-hydroxymethyl-phenoxymethyl)-1-ethyl-propyl]-2-ethyl-phenyl}-5,5,5-trifluoro-4-trifluoromethyl-pent-1-en-3-ol; and mixtures thereof.

20. A regime or regimen for the treatment of a dermatological condition or affliction linked to a keratinocyte or sebocyte differentiation or proliferation disorder, or a keratinization disorder, or a dermatological condition or affliction linked to a keratinization disorder having an inflammatory and/or immunoallergic component, or a cutaneous inflammatory condition or affliction which does not exhibit a keratinization disorder, or a dermal or epidermal proliferation, or bullous dermatoses or a collagen disease, or a sign of skin aging whether photoinduced or chronologic, or a cicatrization disorder or stretch marks, or a disorder of the sebaceous function, or a dermatological condition or affliction having an immunological component, comprising administering to an individual in need of such treatment, a thus effective therapeutic amount of at least one vitamin D analogue as defined by claim 1.

21. A regime or regimen for the treatment of acne vulgaris, comedo-type acne, polymorphic acne, acne rosacea, nodulocystic acne, acne conglobata, senile acne, secondary acne, solar acne, acne medicamentosa or occupational acne, comprising administering to an individual in need of such treatment, a thus effective anti-acne amount of at least one vitamin D analogue as defined by claim 1.

22. A regime or regimen for the treatment of ichthyosis, an ichthyosiform state, Darier's disease, keratosis palmaris et plantaris, leukoplasia, a leukoplasiform state, or cutaneous or mucosal (buccal) lichen, comprising administering to an individual in need of such treatment, a thus effective therapeutic amount of at least one vitamin D analogue as defined by claim 1.

23. A regime or regimen for the treatment of psoriasis, cutaneous, mucosal or ungual psoriatic rheumatism, cutaneous atopy, eczema, respiratory atopy or gingival hypertrophy, comprising administering to an individual in need of such treatment, a thus effective therapeutic amount of at least one vitamin D analogue as defined by claim 1.

24. A regimen or regimen for the treatment of verruca vulgaris, verruca plana, epidermodysplasia verruciformis, oral or florid papillomatoses, proliferations induced by ultraviolet radiation, or baso- or spinocellular epithelioma, comprising administering to an individual in need of such treatment, a thus effective therapeutic amount of at least one vitamin D analogue as defined by claim 1.

25. A regime or regimen for body or hair hygiene, comprising administering to an individual in need of such treatment, a thus cosmetically effective therapeutic amount of at least one vitamin D analogue as defined by claim 1.

26. A pharmaceutical composition comprising a pharmaceutically effective amount of at least one vitamin D analogue as defined by claim 1, formulated into a pharmaceutically acceptable carrier therefor.

27. A cosmetic composition comprising a cosmetically effective amount of at least one vitamin D analogue as defined by claim 1, formulated into a cosmetically acceptable carrier therefor.

28. The pharmaceutical composition as defined by claim 26, formulated as tablets, gelatin capsules, sugar-coated tablets, syrups, suspensions, solutions, powders, granules, emulsions, lipid or polymeric microspheres or nanospheres or vesicles which permit a controlled release, solutions or suspensions for infusion or for injection, salves, creams, milks, ointments, impregnated pads, gels, sprays, lotions, lipid or polymeric microspheres or nanospheres or vesicles, or polymeric patches or hydrogels allowing a controlled release, or collyria.

29. The cosmetic composition as defined by claim 27, formulated as a cream, a milk, a lotion, a gel, a suspension of lipid or polymeric microspheres or nanospheres or vesicles, a soap or a shampoo.

* * * * *